US012708548B2

United States Patent
(12)

Plasencia et al.

(10) Patent No.: US 12,708,548 B2

(45) Date of Patent: Aug. 18, 2026

(54) DEVICE FOR ATTACHMENT TO A SCROTUM

(71) Applicant: ECJ PRODUCTS LTD, Dorset (GB)

(72) Inventors: Elizabeth Plasencia, Dorset (GB); Jeremy Davies, Dorset (GB)

(73) Assignee: BALLDOCO LIMITED, Dorset (GB)

(*) Notice: Subject to any disclaimer, the term of this patent is extended or adjusted under 35 U.S.C. 154(b) by 896 days.

(21) Appl. No.: 17/786,142

(22) PCT Filed: Apr. 6, 2020

(86) PCT No.: PCT/IB2020/053262

§ 371 (c)(1),
(2) Date: Jun. 16, 2022

(87) PCT Pub. No.: WO2021/205198

PCT Pub. Date: Oct. 14, 2021

(65) Prior Publication Data

US 2023/0023794 A1 Jan. 26, 2023

(51) Int. Cl.

*A61H 19/00* (2006.01)
*A61F 5/41* (2006.01)

(52) U.S. Cl.

CPC ............... *A61F 5/41* (2013.01); *A61H 19/32* (2013.01); *A61F 2005/415* (2013.01)

(58) Field of Classification Search

None

See application file for complete search history.

(56) References Cited

U.S. PATENT DOCUMENTS 10,238,527 B1 3/2019 Parmet
10,674,775 B1 * 6/2020 Leigh ..................... A41B 9/023
2008/0127986 A1 * 6/2008 Miller .................. A61F 5/0096 128/883

FOREIGN PATENT DOCUMENTS

GB 2461333 A * 1/2010 ............. A61H 19/00
KR 20100132415 A * 12/2010 ............... A41B 9/08
KR 2016 0058382 A 5/2016
RU 2 022 538 C1 11/1994

OTHER PUBLICATIONS

"International Search Report" in PCT/IB2020/053262, dated Nov. 30, 2020.
"Written Opinion of the International Searching Authority" in PCT/IB2020/053262, dated Nov. 30, 2020.

* cited by examiner

*Primary Examiner* — Thaddeus B Cox
(74) *Attorney, Agent, or Firm* — William H. Bollman

(57) ABSTRACT

The present invention relates to a device for attachment to a male scrotum, specifically for treating erectile dysfunction. The device comprises: a cage having an upper portion which is configured to surround a scrotal septum and two connectors which connect the upper portion to a lower portion and define separate lateral openings through which a left and a right testicle protrude. The two connectors lie in substantially the same plane as a wearer's scrotal raphe when the cage hangs from the scrotal septum; and a body portion extends from the lower portion. The body portion is optionally shaped to resemble a male appendage. Optionally other devices, such as a vibrator, may be fitted inside the male appendage.

19 Claims, 31 Drawing Sheets

38
34

30

80
100
70
36

90
99
18

38
8
16
19
34
18

37a
17

37b
9

30

36

FIGURE 23a
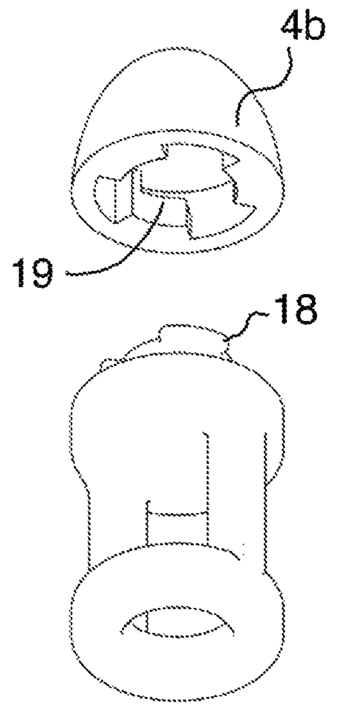
FIGURE 23b
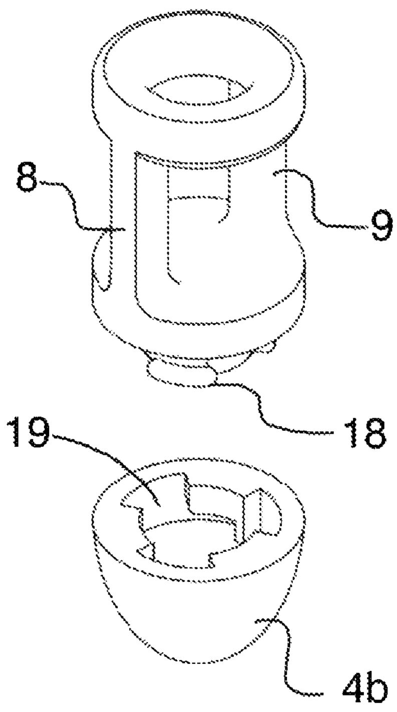
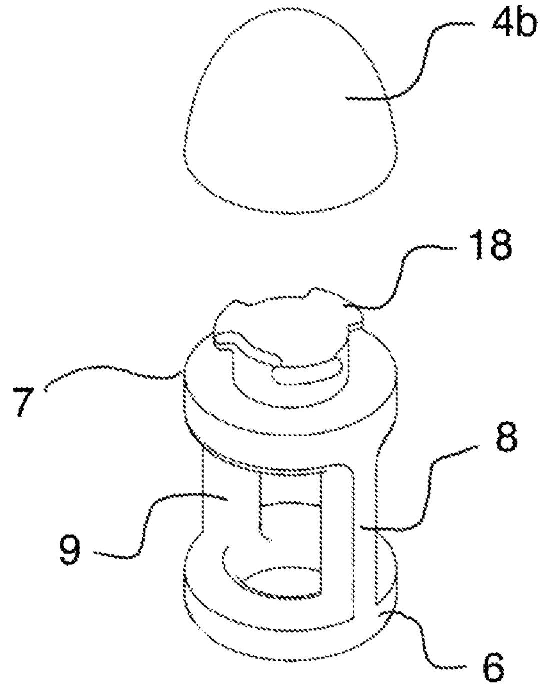
FIGURE 23c

DEVICE FOR ATTACHMENT TO A SCROTUM

FIELD OF THE INVENTION

The present invention relates to a device for attachment to a scrotum, for example for males who may have been diagnosed with and/or suffering from sexual dysfunction, such as for example, erectile dysfunction or premature ejaculation.

BACKGROUND OF THE INVENTION

Symptoms associated with erectile dysfunction (ED) include the occasional inability to obtain a full erection, inability to maintain an erection throughout intercourse, and complete inability to achieve an erection. Lack of morning erections may also be a symptom along with a decrease in sex drive or libido.

The cause of erectile dysfunction may be physiological. For example, the patient may be experiencing erectile dysfunction as a result of suffering from: heart disease, diabetes, high cholesterol, obesity, Parkinson's disease, multiple sclerosis, hormonal disorders (including thyroid conditions and testosterone deficiency), structural or anatomical disorder of the penis, prostate disease, surgical complication, substance abuse, injury in the pelvic area or spinal cord, or radiation therapy. In other cases, the cause of erectile dysfunction may be psychological, for example caused by stress, anxiety and/or depression.

Erectile dysfunction is commonly treated by prescribing drugs such as Vardenafil® or Viagra®. It may however be the case that some men who are experiencing problems with their sexual performance may be reluctant or too embarrassed to seek advice from a medical professional such as a doctor or general practitioner (GP).

Furthermore, mechanical devices such as splints, vacuum pumps with constriction rings, surgical implants have been developed to treat erectile dysfunction. There are however disadvantages associated with these medical devices such as risk of failure, risk of injury, risk of infection, and high associated costs.

Another object is to provide a means for a sexual aid for stimulating a sexual partner.

PRIOR ART

U.S. Pat. No. 3,759,254 (Clark) discloses an hygienic appliance comprising: a resilient and flexible unitary body construction having an elongated thin-walled tubular portion with a rounded closed end portion and an open end. The appliance has a thin-walled scrotum sack portion depending from the tubular portion immediately adjacent the open end. The sack portion includes an opening communicating with an open end of the tubular portion. The interior of the sack portion communicates with the interior of said tubular portion.

Chinese Patent Application CN 2 738 781 (Wang) discloses a testicle air sac physiotherapeutic massaging device which includes a casing, an inflating ball, a deflating valve and an inflating tube. The casing is formed by buckling left and right hemispherical casings through a rotating shaft. Connecting buckles are arranged on side edges of switching openings of the left and the hemispherical casings. The upper parts of the left and the right hemispherical casings are provided with semi-circular gaps. The semi-circular gaps are of a suitable size for receiving a testicle.

US Patent Application 2017/0172784 (Kiefer) discloses an artificial penis for a male person which simulates an enlargement of the smaller erect natural penis. The artificial penis has an interior recess to accommodate an imaginary erect natural penis via an insertion opening. The recess comprises a glans-shaped compartment for the accommodation of an imaginary glans of the erect natural penis, and a penis-shaft-shaped compartment for the imaginary accommodation of the shaft adjoining the glans of the erect natural penis. The artificial penis has a fastening component with a distensible elastic entry opening for part of the scrotum and the testicles, by means of which the artificial penis can be fastened detachably to a wearer.

International Patent Application WO 95/11646 (Jagle) is a sex aid which is adapted to be secured to a penis or taped to a wearer's lower body to be adjusted to the individual anatomy of the sexual partners using special or individual production techniques.

A hollow part is able to receive all penis lengths and can be secured without tapes and is adjustable lengthwise so that the penetration depth of the shaped hollow part can be adjusted.

International Patent Application WO 2007/068988 (Vizkeleti) teaches a therapeutic-sexual appliance for men, which has a self-supporting, hollow portion and an elastic wall. The characteristics of the appliance are that it has a penis holder having shape and surface similar to the penis, ending with a rounded point. A scrotum holder is connected by way of a continuous material transition provided with an elliptic supporting opening on the upper side and a scrotum passing opening on the lower side.

There is a need for a device and a method of treating erectile dysfunction which is accessible to a user without requiring intervention by a medical professional and which is useable by heterosexual and homosexual partners.

There is also a need for a device and method of treatment which can be easily operated by the user without medical intervention and which improves sexual performance, confidence and satisfaction for both partners.

STATEMENT OF INVENTION

According to a first aspect of the present invention there is provided a device for attachment to a scrotum comprising: a cage having an upper portion which is configured to surround a scrotal septum and two connectors which connect the upper portion to a lower portion and define separate lateral openings through which a left and a right testicle protrude, the two connectors lie in substantially the same plane as a wearer's scrotal raphe when the cage hangs from the scrotal septum; and a body portion extends from the lower portion.

Ideally the body portion is removable from, and can be connected to, the lower portion by way of a connection means.

Optionally a phallus or penis shaped portion is adapted to be connected to the cage at a lateral face thereof so as to present the phallus or penis shaped portion so that it lies substantially parallel with an erect or semi erect penis.

In some embodiments the connection means is from the group comprising: a threaded interconnect; a twist lock interconnect, a push-fit interconnect, a snap fit interconnect and a magnetic interconnect.

In a preferred embodiment the upper portion is in the form of a circular ring. In an alternative embodiment the support portion may take other forms such as triangular or another closed loop. Optionally knurling or other stimulators may be positioned around an inner surface of the circular ring or closed loop in order to stimulate the scrotal septum of the wearer.

Ideally the two connectors are substantially rigid. However, they may be flexible or coated in a resiliently deformable elastomer. An advantage with this embodiment is that it may enables a user to open the cage in order to create a larger opening for receiving the scrotum. In an alternative embodiment the cage and/or connectors are elastic or formed in the main from an elastomer material which stretches to receive the scrotum and surround the scrotal septum.

In one particularly preferred embodiment of the device a side connector is provided for connection to a phallus or penis shaped portion. Preferably the side connector includes a means for varying an angle of deployment of the phallus, penis shaped portion or an additional novelty so that it may be located substantially parallel to the wearer's erect penis or deployed through a range of angles from 45 degrees above or below the wearer's penis, for example by way of a universal joint. Optionally the phallus, penis shaped portion or an additional novelty may be repositionable at different heights to enable it to be adjusted to suit each partners. In one embodiment to facilitate this a hinge or bend or a flexing collar may be included in at least the upper portion of the device to assist in varying the angle of deployment of the location of the phallus, penis shaped portion or novelty attachment.

An example is a hinged or slide lock. In the hinged arrangement the slide connector enables the connectors to swing through at least 90 degrees, 45 degrees above and below a notional horizontal plane, to facilitate insertion of the scrotum into the cage as well as help orient the device whilst being worn.

In an alternative arrangement a universal or other flexible joint may connect the appendage to the cage so as to enable the appendage to be manipulated to a desired orientation.

The cage is shaped and dimensioned to receive, retain and substantially surround a portion of the scrotum, and the male appendage may extend beyond one of or each of the first and second opposed ends thereof.

Optionally an additional novelty attachment or phallus may be connected to the cage in order to be deployed in a plane that is substantially parallel to the phallus or simulated penis.

Optionally the upper and lower portions and the connectors are formed from a flexible material which may be overlaid or over moulded with a softer material which is washable and may be coloured and/or textured and/or contoured.

Ideally the upper and lower portions and the connectors are formed as a single injection piece or mould.

In one embodiment the body portion extends from the lower portion is circular symmetric and bulbous shaped. In another embodiment the body portion extending from the lower portion is shaped to resemble a male appendage or novelty device.

Optionally a flexible tether is provided to connect a handle to the body portion. An advantage of this is that the partner of the wearer of the device, or the wearer of the device, may hold the handle in order to assist in its location and in order to stimulate the wearer and or the person with whom the wearer is having intercourse.

In some embodiments an electronic controller may be provided on the handle, via a flexible connector to the device, which includes a cable carrying control signals, to one or more stimulation devices that may be housed in the body portion and/or the cage of the device. The stimulation devices are ideally fitted with batteries which are ideally rechargeable so that batteries can be charged prior to use.

Optionally a vibrating means is provided in the body portion. The vibrating means may also have a rechargeable battery is provided that is sealed within the body portion.

Optionally a stimulator or tickler may be attached to an underside of a cap that connects the connector or tether to the device or to the attachment (phallus itself), so that erogenous zones of the person being penetrated are touched and tickled thereby intensifying stimulation. Where a handle is present the person may, when desiring deeper penetration or thrusting, apply a gentle tugging action using the handle which may also intensify stimulation where a stimulator or tickler is attached.

In another preferred embodiment the cage may be adapted to receive a removable stimulator (not shown) which is ideally fitted to (or formed integrally with) the cage, cap, flexible cord or one embodiment of the phallus. Such a stimulator is typically located in or on the fore portion of a cage connector or around the phallus so as enhance stimulation to the person being penetrated.

In some embodiments a remote control means enables an operator to control the speed and/or intensity of the vibrating means. A separate remote controller may be provided, or the remote controller may be fitted into the handle or at some other location of the device.

The remote control means may incorporate a wireless communications device, such as a transmitter operating using Bluetooth® wireless protocol. In some embodiments a mobile communications device may be provided with application specific software (also knowns as an APP) which operates on the mobile communications device, such as a smart phone or tablet. Such mobile communications devices normally have displays which present a menu of choices or operational modes to users as well as images.

Therefore a system may include software for use with a mobile communications device, which when operating on the mobile communications device configures the mobile communications device into a remote controller. When so configured, the mobile communications device may include voice recognition software which enables users to speak commands to the mobile communications device for relaying as an instruction, via a wireless communication channel, to a vibrator or stimulator. Such voice recognition software when used in conjunction with application specific software, may assist users of the device to improve and enjoy sexual intercourse. This is especially the case, for example where one or more partners has a physical injury or limited mobility and may require assistance with such intimate matters.

In an alternative embodiment of the device there is included a handle and connection means for removable attachment to the body portion thereby enabling a partner of the wearer to control the device by way of a manual pressure switch or other controlling actuator.

Optionally an electro stimulator is provided on the cage and/or first body or phallus. Alternatively the electro stimulator is provided on the attachment and is operable to be used by a partner of the wearer via a remote control means, which as mentioned above, may be wirelessly operable or may connect to the stimulator via a wire contacting the flexible connector.

The vibrator and/or electro stimulator may likewise be controlled by the partner of the wearer via a remote device which may be wirelessly operable or may connect to the stimulator via a wire contacting the flexible connector.

In another embodiment the body portion may comprises at least one inflatable portion which is configured to be inflated or deflated in order to adjust its dimensions to suit at least one of the partners.

Optionally there is provided a kit which includes a plurality of body portions that are configured to be releasably engageable one with another and preferably releasably connected to the device prior to intercourse.

The invention may therefore be provided in a modular form with detachable body portions and attachments so that, for example, a user is able to purchase a basic kit and subsequently purchase separate sized and shaped appliances and attachments in order to suit a certain taste or physiological proportions or desire. For example, some couples might prefer a larger phallus whereas others may prefer a phallus of different shape or proportions or flexibility or with stimulating means housed therein.

The body portion or attachment may have any suitable structure and/or dimensions and/or shape depending on the requirements of the device. In one embodiment the body portion may be hollow.

In one embodiment, the body portion is elongate in shape, for example generally tubular or phallus in shape, having a first end and a second opposed end.

The body portion may define a longitudinal axis extending between the first and second opposed ends thereof. Ideally the body portion is dimensioned and shaped to resemble a penis and is formed from a resiliently deformable material which is able to stimulate its recipient during sexual intercourse. A bulbous end is preferably provided on the second portion in order to simulate a glans portion of the male appendage. Optionally the bulbous end is removable and replaceable with different sized and shaped bulbous ends.

According to a second aspect of the invention there is a provided a device for attachment to a scrotum comprising an outer cage that comprises two or more portions that are separable and reconnectable to define a cavity, the portions have first and second opposable ends and at least one pair of opposable side portions extending therebetween, the cage being configurable between: a first open configuration, in which the at least one pair of opposable side portions are separated from each other to define a cavity which receives the scrotum; and a second closed configuration in which the at least one pair of opposable side portions of the cage structure are substantially in contact with each other thereby surrounding the wearer's scrotal septum.

A further opening preferably extends in a plane extending substantially perpendicular to the plane defined by the openings of the first and/or second ends of the cage or wall structure.

In one embodiment, the cage is resiliently biased to the first open configuration. For example, the cage may be resiliently biased by a spring or elasticated mechanism to the first open configuration.

Optionally at least a first body portion is preferably releasably engageable with the cage so that at least one connector or fastener is configured to retain the first body portion.

The body portion may be releasably attachable to the cage by any suitable mechanism including but not limited to push-fit or snap fit engagement or threaded engagement. For example, the body portion may comprise a threaded portion configured for threaded engagement with a threaded portion provided on part of the cage.

The body portion may extend from or be releasably engageable to any suitable portion of the body portion. In one embodiment, the body portion extends from one of the first or second opposed ends of the body portion.

The cavity may have any suitable shape and/or dimensions depending on the requirements for the device. In one embodiment, the body portion is adjustable to provide a cavity having predetermined dimensions to provide a snug fit for surrounding and receiving the scrotum. The dimensions and/or shape of one or more portions, for example the whole, of the cavity may be adjustable.

Optionally in one embodiment, the body portion comprises at least one inflatable portion located adjacent at least a portion of the cavity defined therein, and in which the at least one inflatable portion is configured to be inflated or deflated in order to adjust the dimensions of the adjacent portion of the cavity.

The inflatable portion(s) may be located at any suitable location on the body portion. The body portion, or cage structure, preferably comprises an inner surface extending between the first and second opposed ends thereof. The inflatable portion(s) may be located at or adjacent one or more of the first and second opposed ends thereof and/or adjacent the inner surface thereof and adjacent the cavity.

The body portion may have any suitable shape and dimensions depending on the requirements for the device. For example, the body portion may be shaped and dimensioned to resemble a male appendage, such as for example a model or replica penis, or a sex toy or other attachment.

Optionally an attachment may include a vibrating means, such as motor which is operated with an eccentrically located mechanical weight which when rotates at speed provides a thymic pulsing or vibrating force which is transmitted along the attachment.

Electro stimulators use very small electrical signals to stimulate the body. These electric signals may be controllable or generated at random. They are ideally applied to the skin of one or both partners and may be applied via surfaces of one of the aforementioned attachments, such as the phallus (so that the person being penetrated can be stimulated) or via portions of the cage so that the person wearing the device, may experience stimulation to the scrotum and/or testicles.

In another embodiment an external surface of the attachment may be ribbed or patterned or contoured in order to resemble a penis as well as to provide additional stimulation to the wearer's partner.

Ideally the device is shaped to resemble a male appendage and configured to be worn by a wearer, the device is connected to a handle by way of a connector, the handle is for use by the wearer's sexual partner or the wearer himself such that in use the partner is able to control the device as mentioned above. Therefore by pulling the handle the phallus may be pulled into the person being penetrated, to simulate the thrusting of an erect penis, thereby providing sexual stimulation to a partner of someone suffering from erectile dysfunction.

The body portion of the device may be formed from any suitable washable and soft touch material that is suitable for adult toys and sex aids. For example, the first body portion may be made of one or more of: metals (such as stainless steel, aluminium, gold and/or silver), silicone, elastomer, thermoplastic rubber, hard ABS plastic or any combination thereof.

Embodiments of the present invention, will now be described in more detail and by way of example only, with reference to the drawings, in which:

BRIEF DESCRIPTION OF THE FIGURES

FIGS. 11*a* to 12*e* show overall views of components of the embodiment in FIGS. 10*a* to 10*d* when disassembled;

FIGS. 23*a* to 23*f* show views of a similar device shown in FIGS. 22*a* to 22*f*, formed as a two part mould with a removable tip, and depict overall views (FIGS. 23*a* and 23*b*) from below and (FIG. 23*c*) from above, the Figures showing interconnection means which connect the tip to the cage;

FIGS. 28*a* to 28*f* show views of an alternative embodiment of the device with a hinged connector as part of the cage, formed as a single mould and shows above and under plan views (FIGS. 28*a* and 28*e*), a side elevation view depicting the hinged connector (FIG. 28*b*) and side elevation views (FIGS. 28*c* and 28*d*);

DETAILED DESCRIPTION OF PREFERRED EMBODIMENTS

Figure 1:
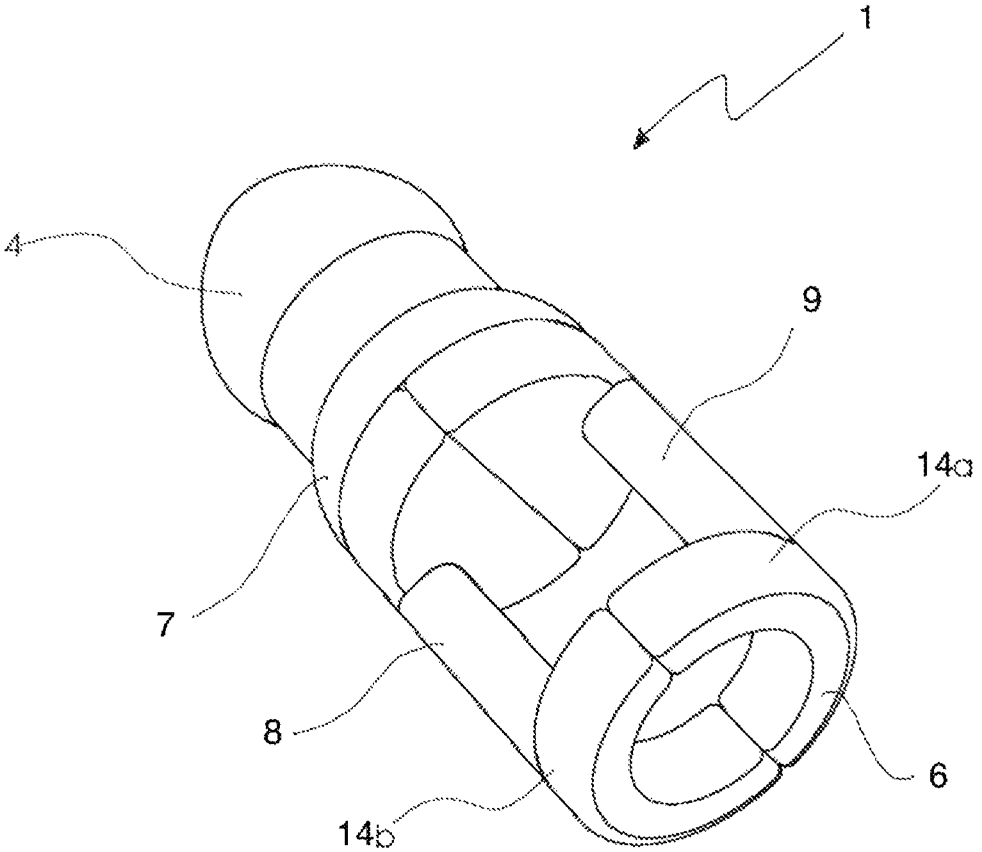
FIG. 1 is an overall perspective view of one embodiment of the device of the present invention and shows a cage and a lower portion.
Figure 5A:
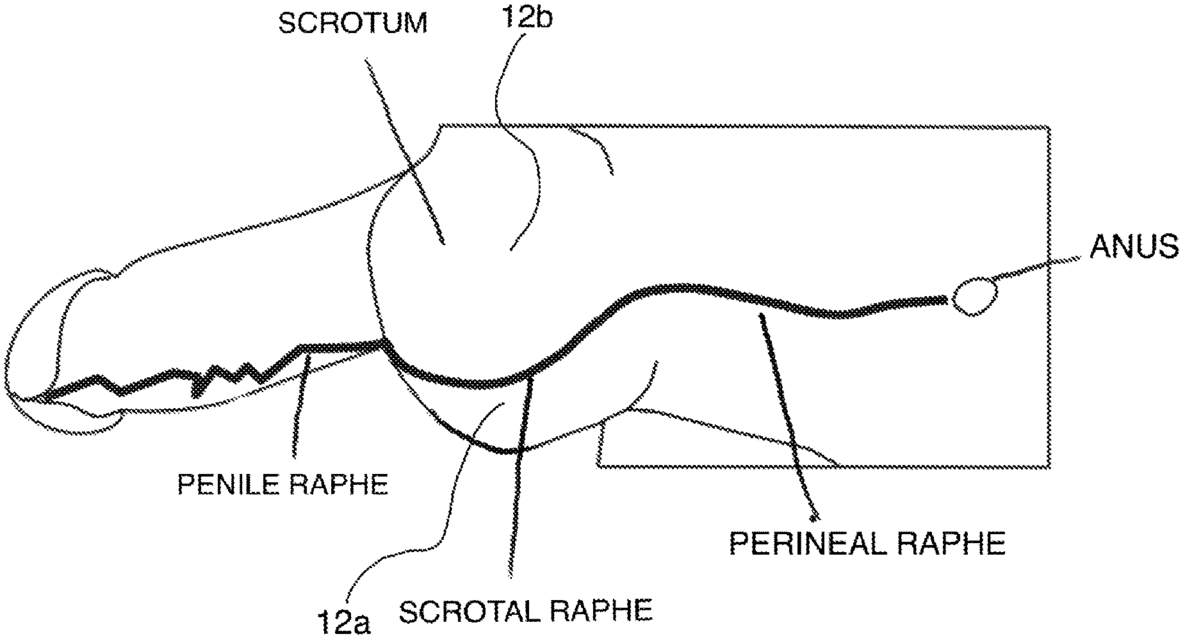
FIG. 5*a* is diagrammatical view of a scrotum and shows the location of the cage around a scrotal and a line defining the scrotal raphe.
Figure 5B:
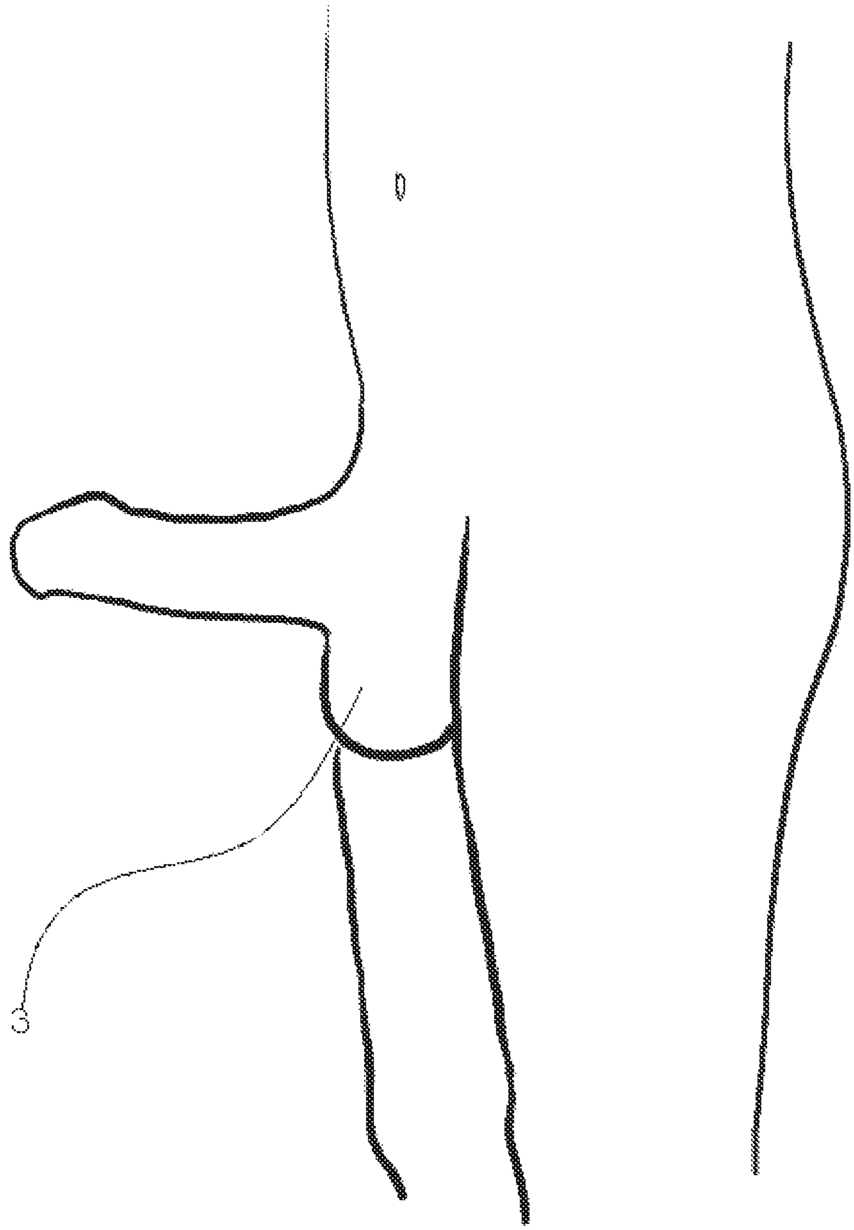
FIG. 5*b* is diagrammatical view of an erect penis and scrotum and shows testicles and a line defining the scrotal raphe.

With reference to the Figures generally and specifically FIGS. 1, 5*a* and 5*b* there is shown a device 1 for attachment to a scrotum 3 so that a wearer's testicles 12*a* and 12*b* (FIGS. 5, 12 and 17) protrude either side of a cage 14 for treatment of erectile dysfunction.

The device 1 comprises a cage 14 which is defined by an upper portion 6 that is configured to surround a scrotal septum (FIG. 6) and a left hand connector 8 and a right hand connector 9 which connect the upper portion 6 to a lower portion 7 which in use touches the scrotal raphe (FIG. 5*a*).

The connectors 8 and 9 define separate lateral openings through which a left testicle 12*a* and a right testicle 12*b* protrude. The two connectors 8 and 9 lie in substantially the same plane as a wearer's scrotal raphe (FIG. 5*a*) when the cage 14 hangs from the scrotal septum (FIG. 5*a*). A bulbous portion 4 extends from the lower portion 7. The bulbous portion 4 may be formed integrally with the lower portion 7 of the cage 14.

As can be seen from the Figures the device 1 may be formed from a metal, (such as aluminium, gold and/or silver), but is ideally formed from stainless steel. However, it is to be understood that the device may also be formed from any suitable material such as silicone rubber, an elastomer, a thermoplastic rubber, a rigid acrylonitrile butadiene styrene (ABS) or other synthetic plastics material or a combination of the aforementioned materials.

Figure 2:
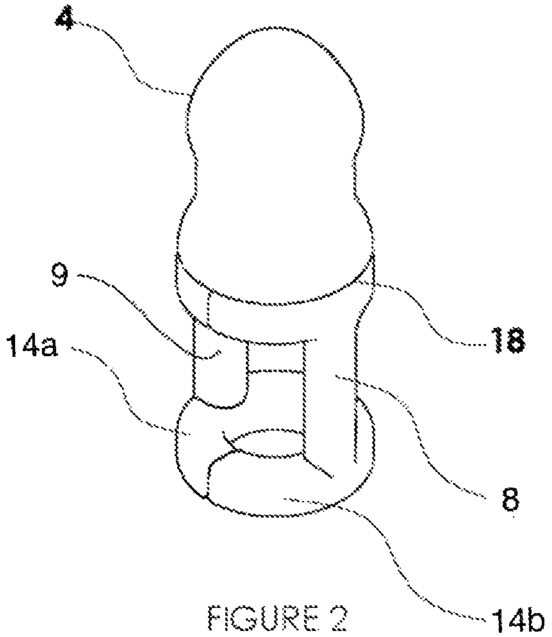
FIG. 2 is an overall view from above of the device of FIG. 1 and shows the cage connected to the lower portion.
Figure 3:
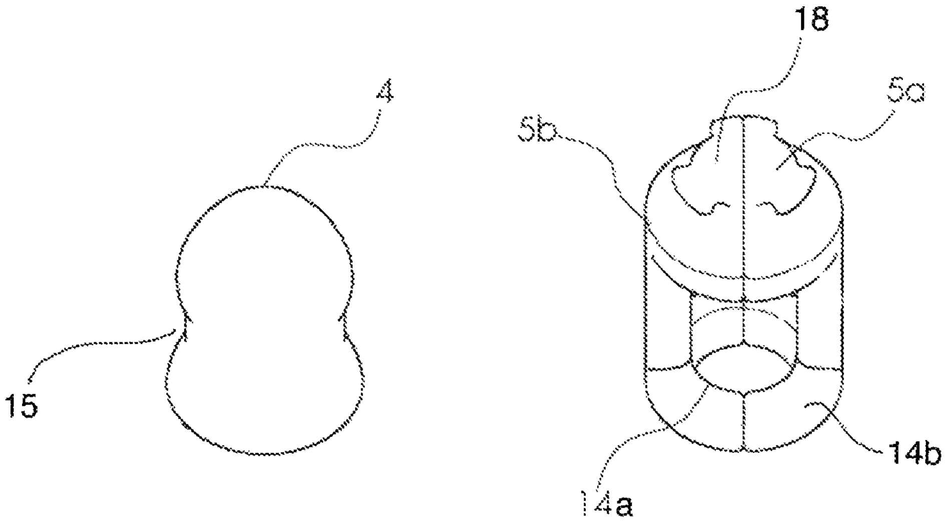
FIG. 3 shows views of the device of FIGS. 1 and 2, when dissembled and depicts the upper body portion (left hand image) and left and right interconnected pieces (right hand image) that form the cage.
Figure 4:
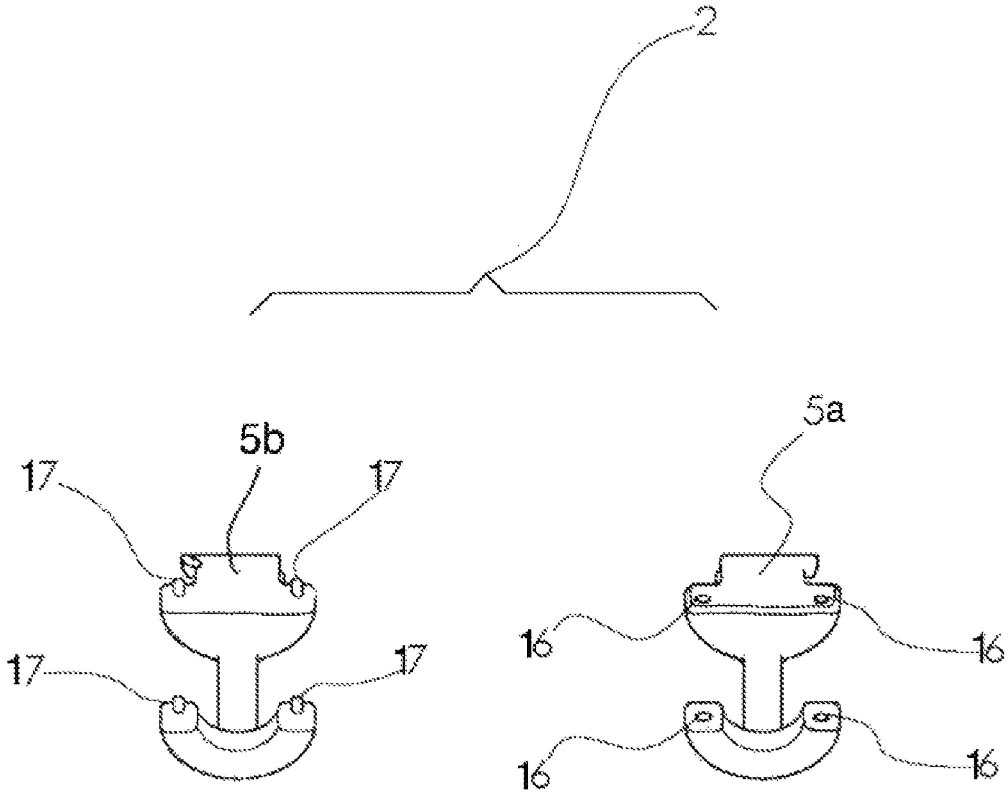
FIG. 4 shows view of the left and right interconnected pieces, when fully separated and depicts pips and recesses which enable the left and right interconnected pieces to inter-engage.

As shown in FIGS. 2 to 4, the device 1 is separable into three portions: a fore cage portion 14*a*, an aft cage portion 14*b* and a lower body portion 7. Each of these are discussed in turn and with reference to the Figures in which like parts bear the same reference numerals. It is appreciated that one or more of these separate portions may be formed integrally with another or both the other cage portions 14*a* and 14*b*.

The fore cage portion 14*a* and the aft cage portion 14*b* are releasably engageable with each other, by way of pips 17 which locate into recesses 16 so that the two cage portions 14*a* and 14*b* locate and connect one to one another. In the embodiment shown in FIGS. 2 to 4 the body portion 2 has a connection means 18 which is defined by a three part form that engages into a similar shaped recess (FIG. 8*c*) twists and locks in place. Other types of connection means may include a threaded interconnect and/or a twist lock interconnect and/or a push-fit interconnect and/or a snap fit interconnect and/or a magnetic interconnect. It is appreciated that a range of different attachments may be connected to the cage 14.

It can be seen from FIGS. 1 to 7 that the cage portions 14*a* and 14*b* comprise cooperative engagement features in the form of pairs of male 17 and female 16 engagement features for connecting the cage portions 14*a* and 14*b* together. It is however to be understood that the cage portions 14*a*, 14*b* may be releasably engageable using any suitable means including but not to be limited to magnets, hook and loop fasteners, or any combination thereof.

Figure 6:
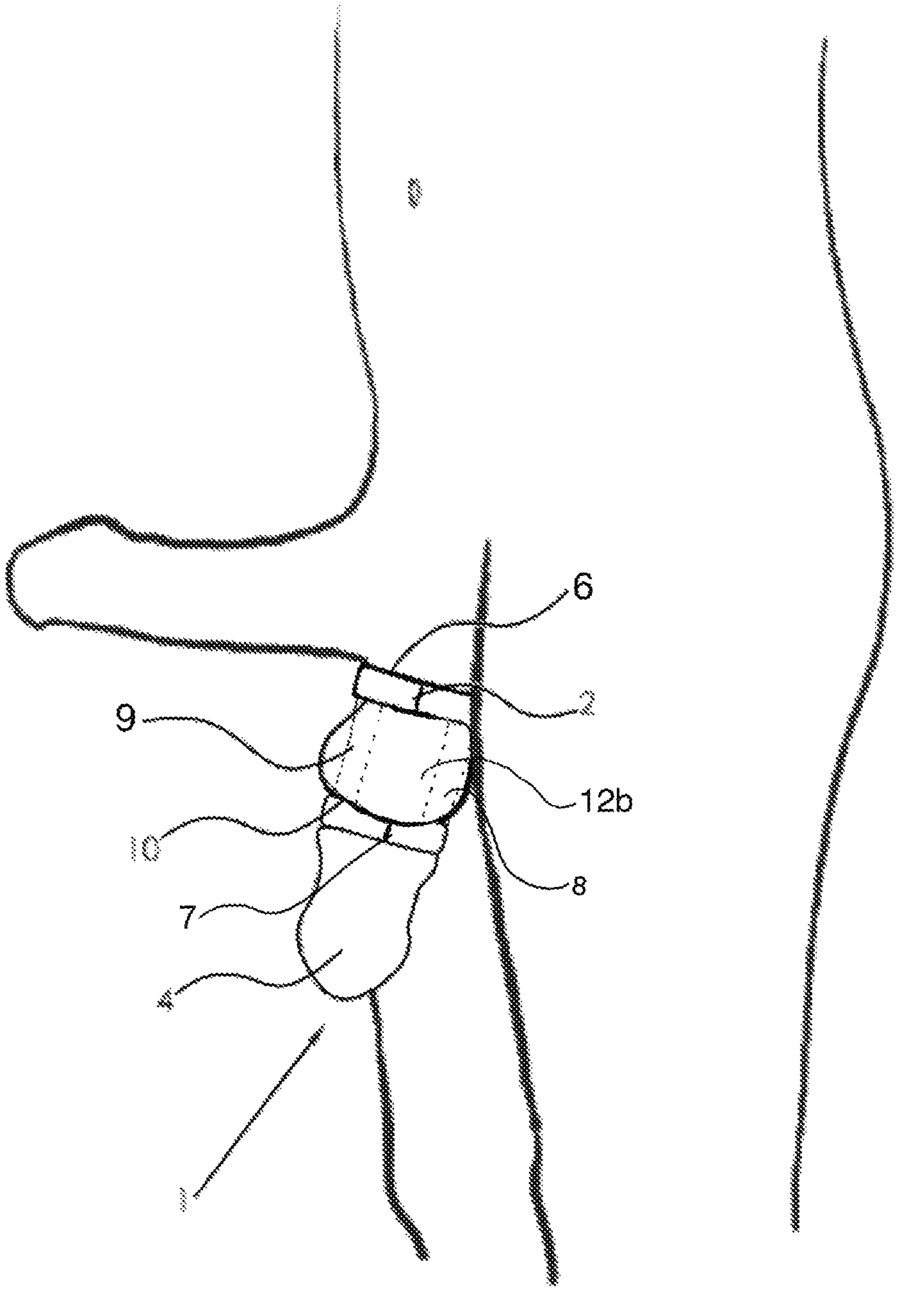
FIG. 6 is diagrammatical view of an erect penis and scrotum with the device of FIG. 1 assembled and attached to, and in hidden detail the supports hanging from, the scrotum.
Figure 7A:
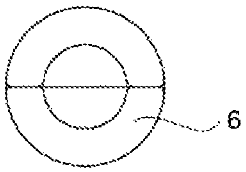
FIGS. 7*a* to 7*e* show end elevations (FIGS. 7*a* and 7*e*), side elevations (FIGS. 7*b* and 7*c*) and an overall view (FIG. 7*d*) of the device of FIG. 1.
Figure 7B:
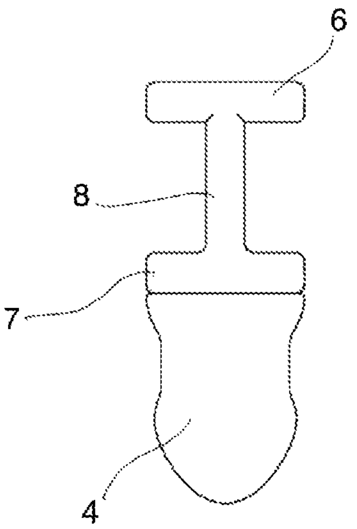
Figure 7C:
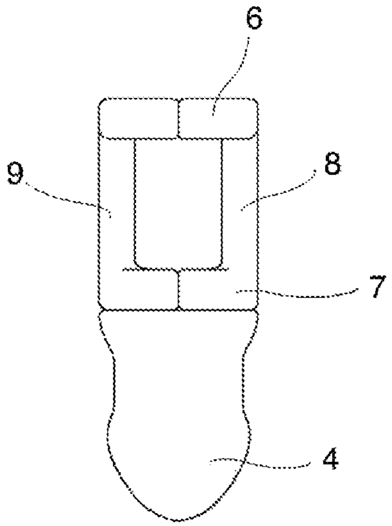
Figure 7E:
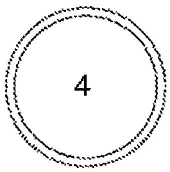
Figure 7D:
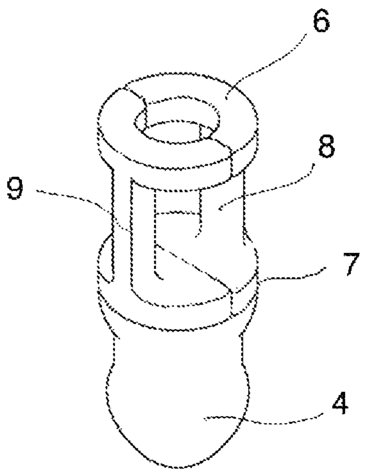

Each cage portion 14*a*, 14*b* has a connector that extends from a lower to an upper region of the cage when assembled. There are two connectors: a left hand connector 8 and a right hand connector 9. Once assembled the cage portions 14*a* and 14*b* connect by way of the pips (male engagement features 16) and recesses (female engagement features 17). When connected together the cage portions 14*a* and 14*b* define a cavity for receiving and retaining the scrotum as shown in FIG. 6. In the illustrated embodiment in FIG. 7 shows a body portion 4 which is elongate in shape with a bulbous tip 4.

Figure 15:
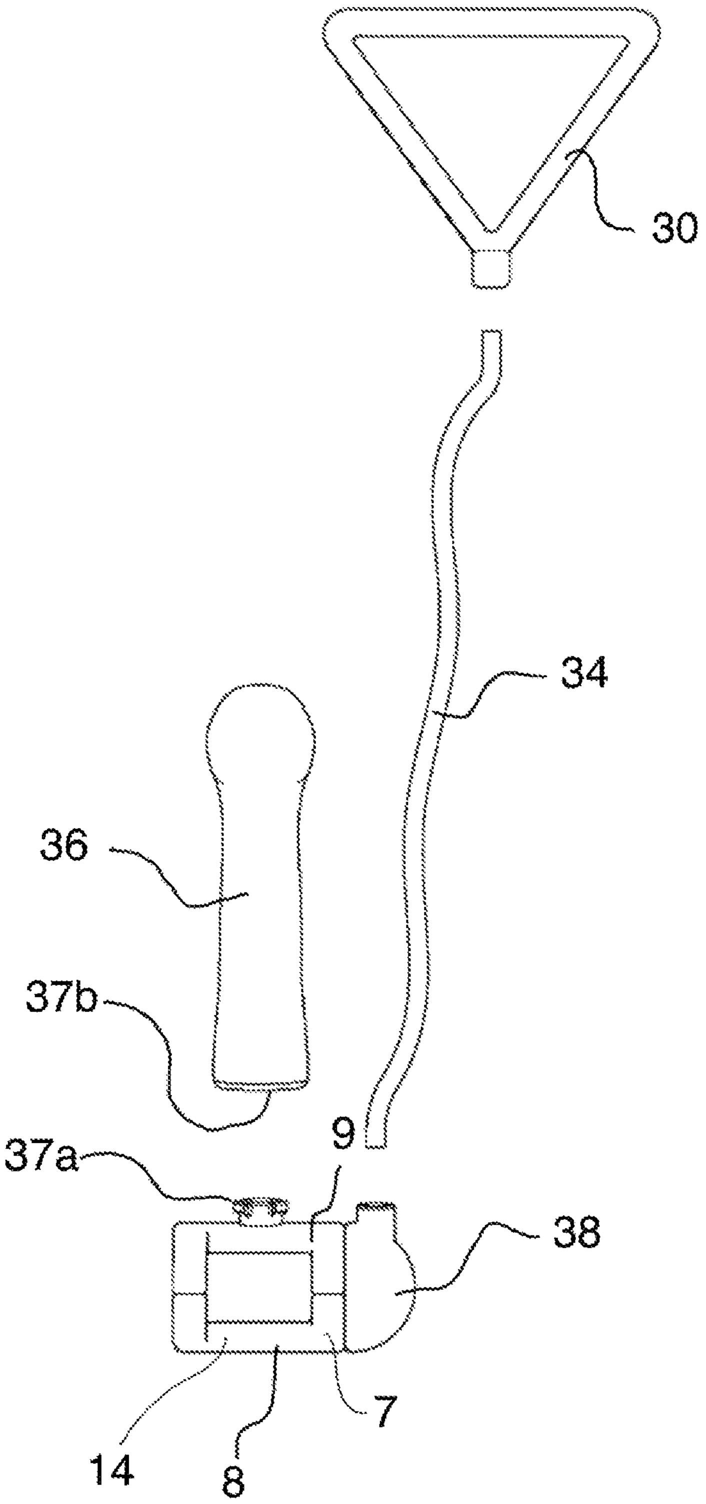
FIG. 15 shows an image of a kit in a disassembled form which includes an embodiment of the invention, a phallus, a flexible connector and a handle.

It can be seen in FIGS. 1 and 10*a*, 10*b* and 10*c* that the cavity, defined by the cage 14, extends between an upper portion 6 and a lower portion 7. Referring to FIG. 15, a phallus 36 extends from a side of the cage 14 and engages removably with the cage 14 by way of a twist interconnect 37*a* formed in an end of the phallus which engages with a similar interconnect 37*b* formed on the side of the cage 14. The engagement features 37*a* and 37*b* secure the phallus 36 or dildo onto the cage 14.

It can be seen from the Figures that the body portion 4 is shaped to resemble a penis. It is however to be understood that the body portion 4 may have any suitable shape and/or dimensions depending on its particular requirements.

In another embodiment the body portion 4 has a first end providing an engagement feature 18 (shown in FIG. 8*c*) is configured for releasable engagement to the engagement feature 19 of the body portion. In the illustrated embodiment in FIGS. 8*a*, 8*b* and 8*c*, the engagement feature 19 of the body portion 4 is in the form of a recess shaped and dimensioned to receive and to provide rotatable, releasable engagement with the engagement feature 18 of the body portion 2. It is however to be understood that the first portion may be secured to the cage 14 by any suitable means. In one embodiment, the body portion 4 may be permanently engaged with or formed integrally with the body portion 4.

In use, a user (shown diagrammatically in FIG. 6) places his scrotum in the cage 14 and the testicles splay and protrude through the lateral openings defined on each side between the left hand 8 and right 9 hand connectors. The scrotum (scrotal sack) extends through lateral openings defined in the cage 14 as can be seen in FIG. 6. The user may then deploy the second body portion as a bulbous phallus 4 (as shown in FIG. 6) or as a separate dildo (as shown for example in FIGS. 10 and 17).

In the embodiments shown in FIGS. 7, 10, 12 and 23 for example, the user secures the body portion 4 to the cage 14, for example by twisting and rotationally engaging the engagement features 18 and 19 provided by the body portion 4. The device 1 once assembled in some embodiments is configured to resemble a male appendage, in this case a penis, and as such addresses the issue of erectile dysfunction.

Figure 8A:
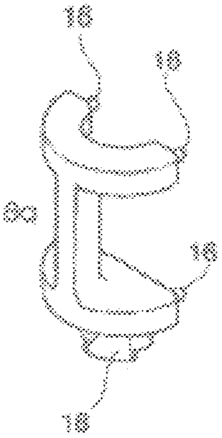
FIGS. 8*a* to 8*c* show views of the cage of the device of FIG. 7, from above when disassembled (FIGS. 8*a* and 8*b*) depicting pips and recesses which enable fore and aft cage pieces to inter-engage one with another and an overall view of the underside of upper portion and its locking mechanism (FIG. 8*c*)
Figure 8B:
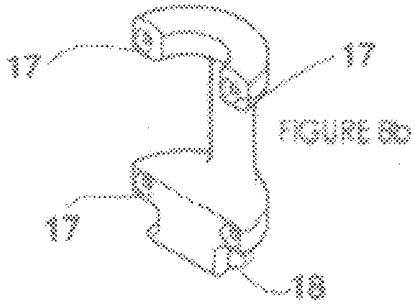
Figure 8C:
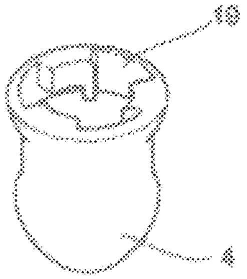

FIGS. 7*a* to 7*e* show an end elevation, side elevations and overall views of the device of FIG. 1. FIGS. 8*a* to 8*c* show views of the cage of the device of FIG. 7, from above when disassembled and depicts pips and recesses which enable fore and aft cage pieces to inter-engage one with another.

Figure 9A:
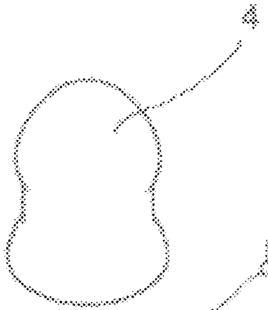
FIGS. 9*a* to 9*c* show views from below of the device of FIG. 7 when disassembled and shows inter-locking mechanisms formed in the left and right interconnect component pieces (FIGS. 9*b* and 9*c*) and an overall view of the upper portion (FIG. 9*a*) from above.
Figure 9B:
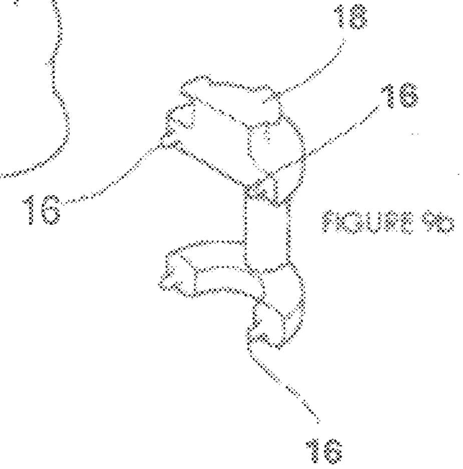
Figure 9C:
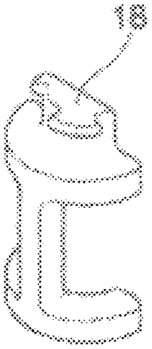

FIGS. 9*a* to 9*c* show views from below of the device of FIG. 7 when disassembled and show an inter-locking mechanisms formed in the left and right interconnect component pieces.

Figure 10A:
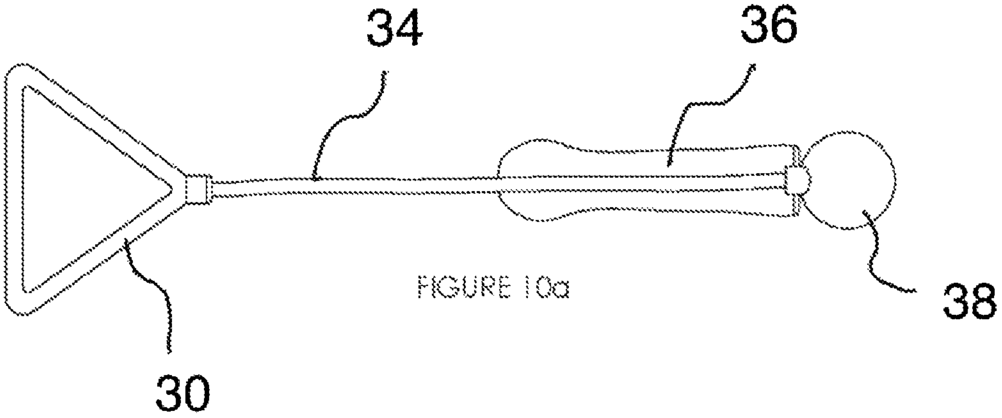
FIGS. 10*a* and 10*b* show plan and elevation views of an embodiment of the device with a flexible connector and a handle and shows a phallus connected to the cage of the device.
Figure 10B:
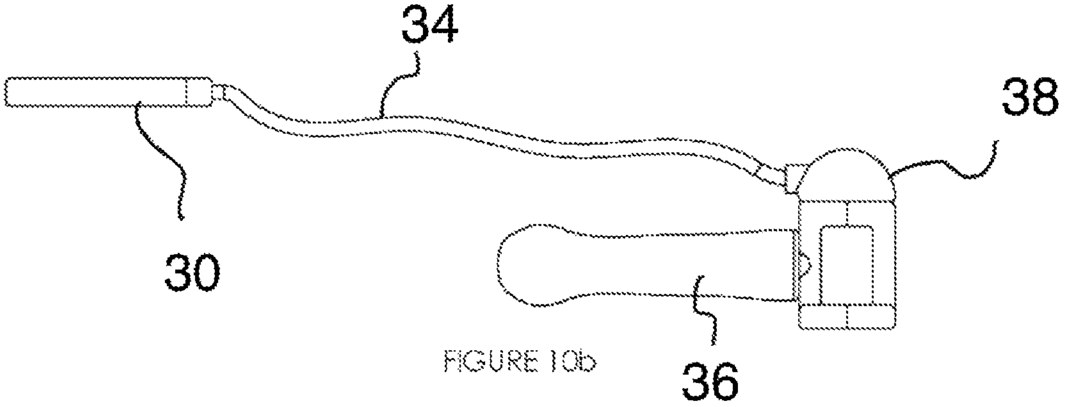
Figure 10C:
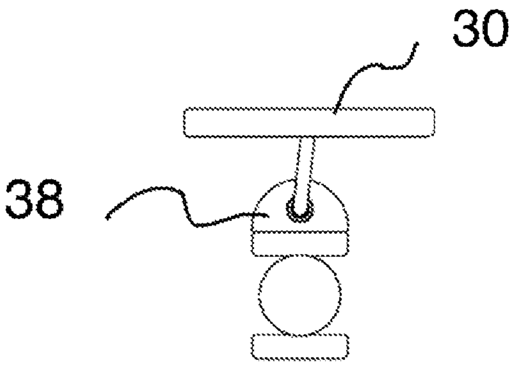
FIGS. 10*c* and 10*d* show end views of the embodiment depicted in FIGS. 10*a* and 10*b;*
Figure 10D:
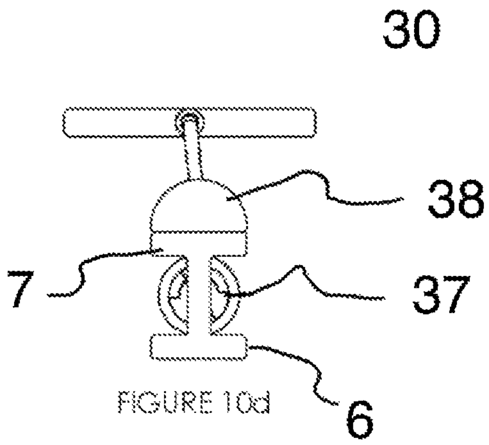

FIGS. 10*a* and 10*b* show plan and elevation views of an embodiment of the device with a flexible connector and a handle. FIGS. 10*c* and 10*d* show end views of the embodiment in FIGS. 10*a* and 10*b* and shows a phallus connected to the device.

Figure 13:
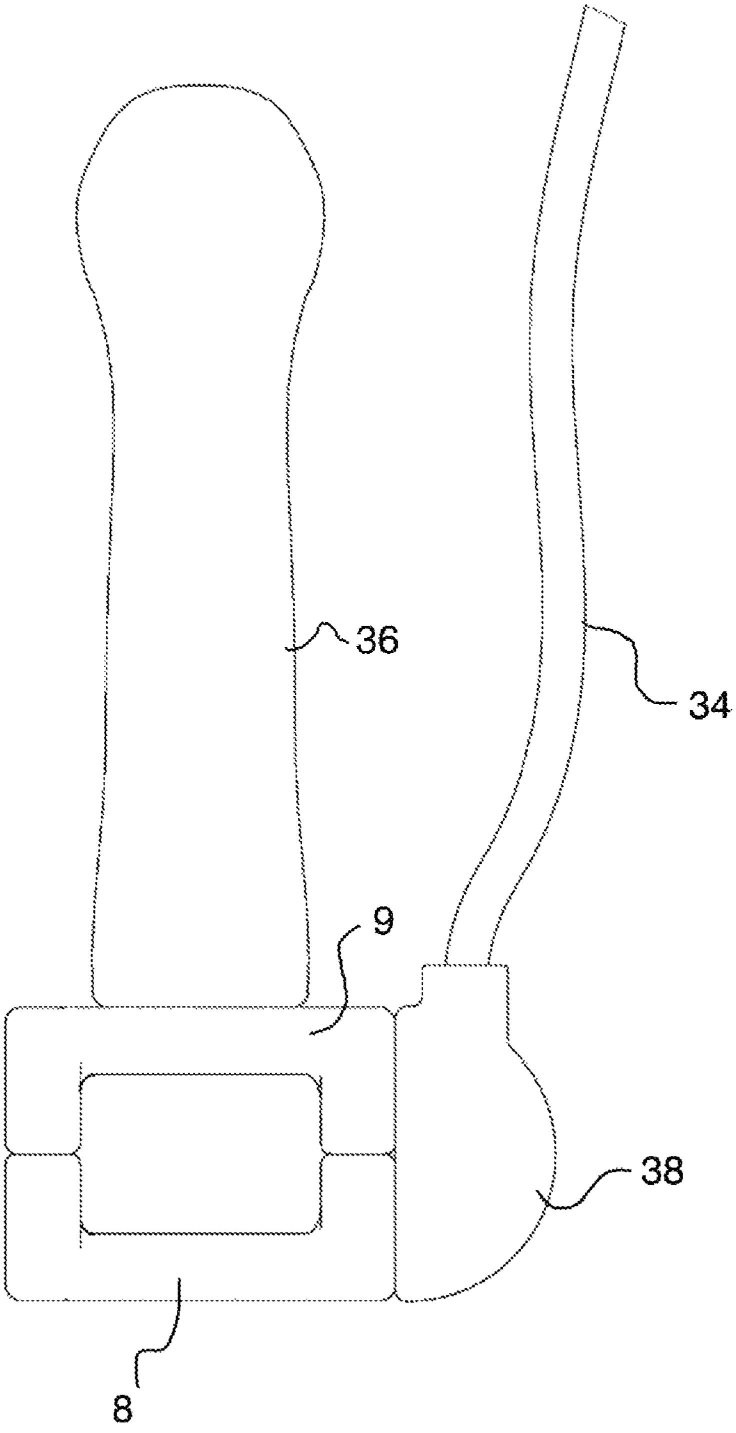
FIG. 13 shows an enlarged side view of the invention with a phallus attached to a wall of the cage that defines the cavity for receiving the scrotum (not shown)

FIGS. 11*a* to 12*e* show overall views of components of the embodiment in FIGS. 10*a* to 10*d* disassembled. FIG. 13 shows an enlarged side view of the invention with a phallus attached to a wall of the cage that defines the cavity for receiving the scrotum (not shown).

Figures 11, 11A, 11E, 12A, 12B, 12C, 12D, 12E:
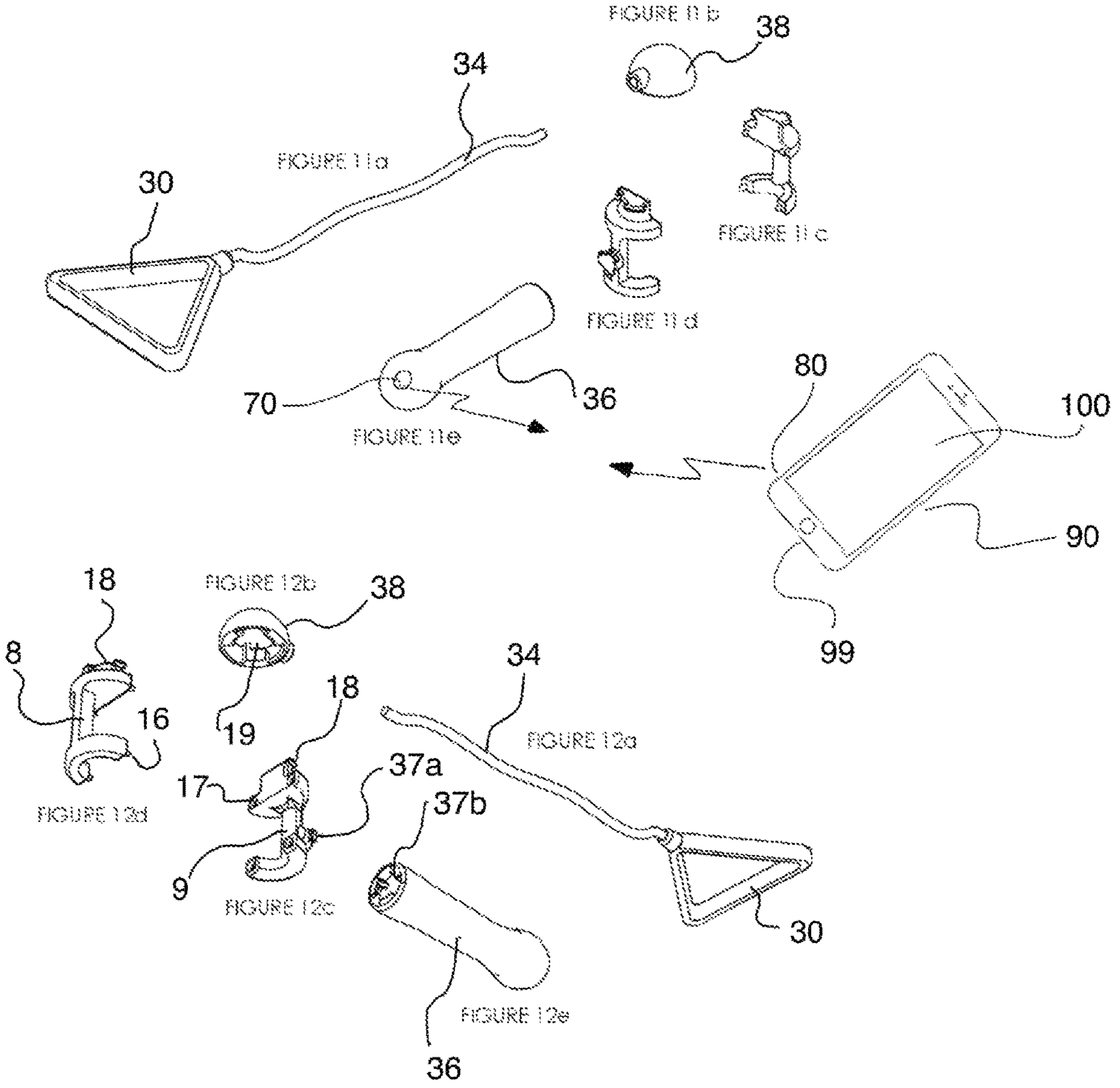

In FIG. 11*e* there is shown a system that includes the device 1 and a phallus 36 which has a vibrator or vibrating device (not shown) embedded in it. The phallus 36 has a wireless receiver 70 which operates using wireless communication protocol, such as Bluetooth® to receive a signal from a mobile communications device 90.

The mobile communications device 90 has a display 100 and is provided with application specific software which configures the mobile communications device 90 to display a menu of choices or operational modes on its display 100 to a user. The mobile communications device 90 is configured to be operable in a voice recognition mode to enable a user to speak a commands to a microphone 99 so that the mobile communications device 90 relays an instruction, via the wireless communication protocol, to the receiver 70 to actuate the vibrator (not shown). Although reference has been made to a vibrator it will be appreciated that an instruction may be transmitted to actuate electrodes of an electro stimulator (not shown).

In an alternative embodiment remote communication may be achieved between one person to a remotely located vibrator or an electro stimulator, for example via an Internet connection or by using a suitable operator interface, such as a mouse (not shown) or a mobile communications device operating under control of a voice recognition software. An instruction or request may be transmitted to actuate a vibrating device and/or electrodes of an electro stimulator.

Figure 14A:
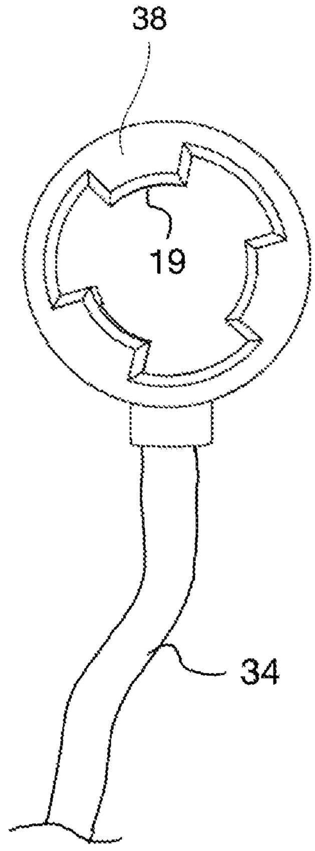
FIG. 14 shows an end view (FIG. 14*a*) and an overall side view (FIG. 14*b*) of the cage with a twist lock for connecting a body portion or an appendage to the cage defining the cavity.
Figure 14B:
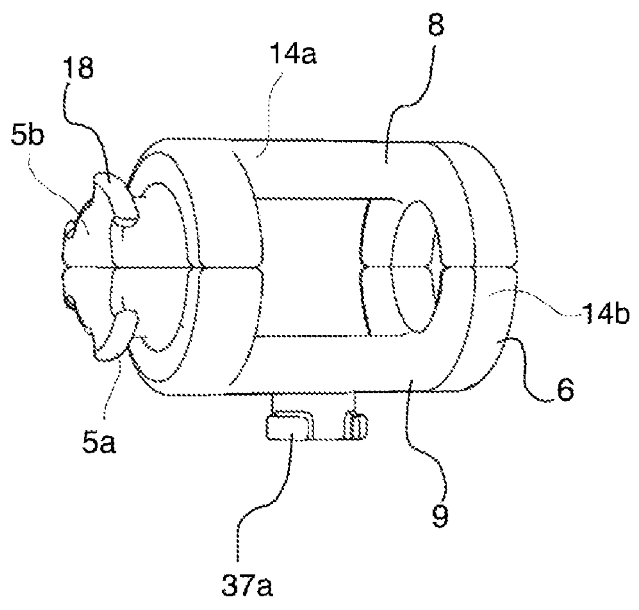

FIG. 14 shows an end view (14*a*) and an overall side view (14*b*) of the cage with later inter-engager for connecting an appendage to the cage defining the cavity.

Figure 16:
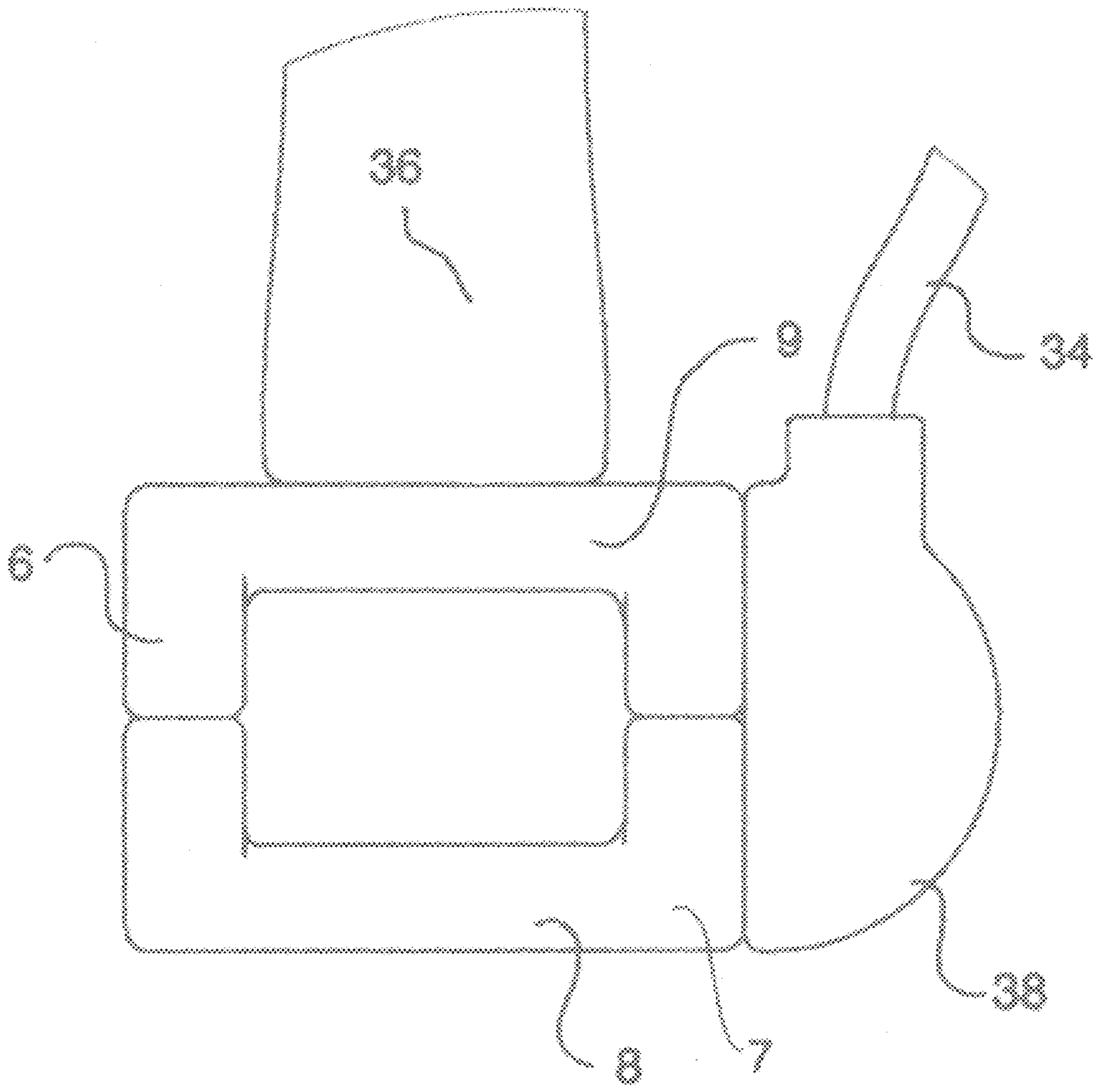
FIG. 16 is a close up view showing where the phallus (or another appendage) is connected to the cage defining the cavity and depicts a cap to which a tether and handle are connected.

Referring briefly to the embodiment shown in FIGS. 15 and 16 this embodiment further assists a partner to pull on a handle 30 which is connected to the device 1 has a forward connector portion 8 and an aft connector portion 9 which may comprise at least one flexible linkage or flexible connector which stretch to receive a wearer's scrotum.

In a further optional embodiments, for example as shown in FIG. 15 a kit or system is provided which is shown in a disassembled form. The kit ideally includes: one embodiment of the invention, a male phallus 36, a flexible connector 34 and a handle 30.

Figure 17:
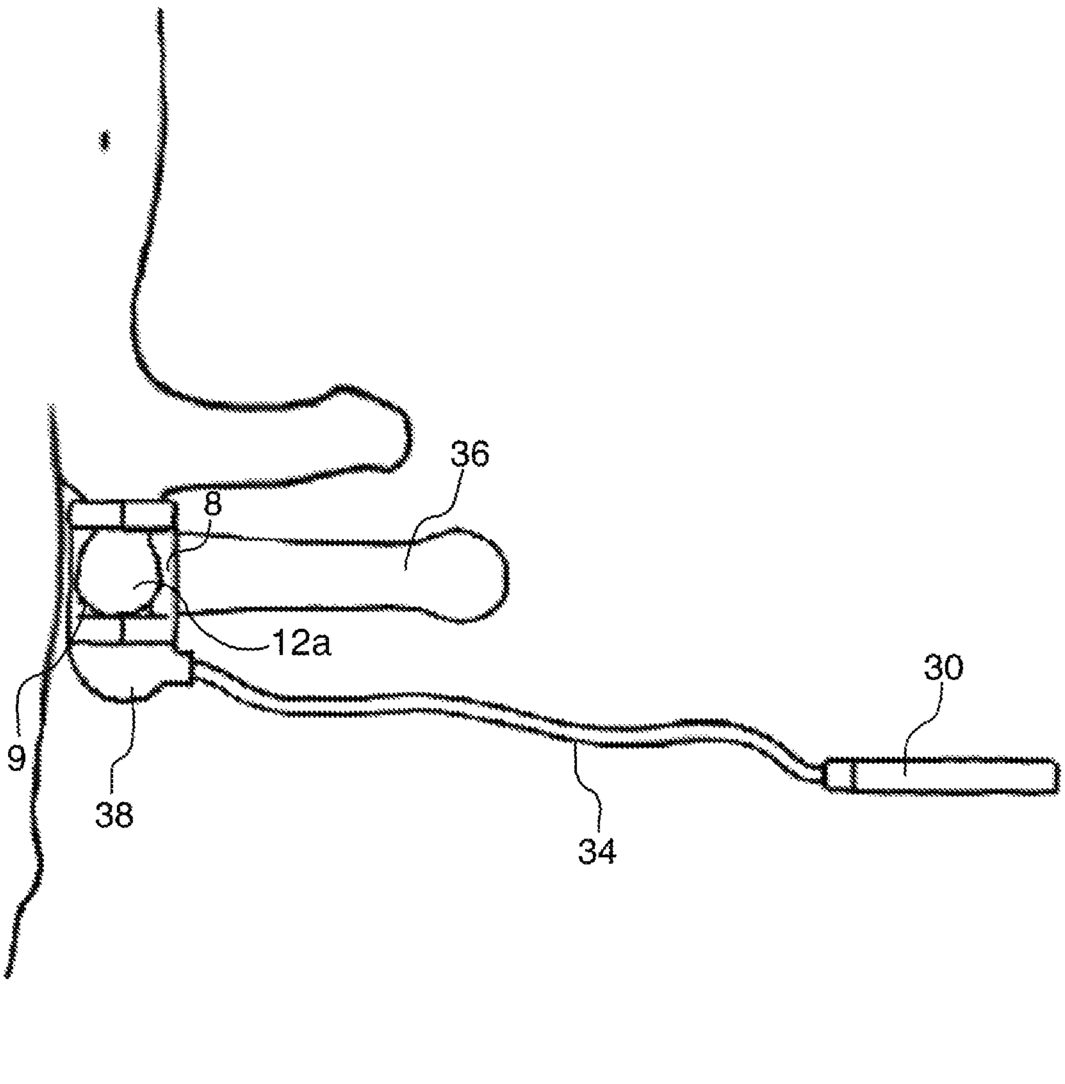
FIG. 17 is a diagram showing how the device is deployed and hangs from the wearer's scrotum, the location of the appendage (male phallus), the flexible connector and handle.
Figure 18A:
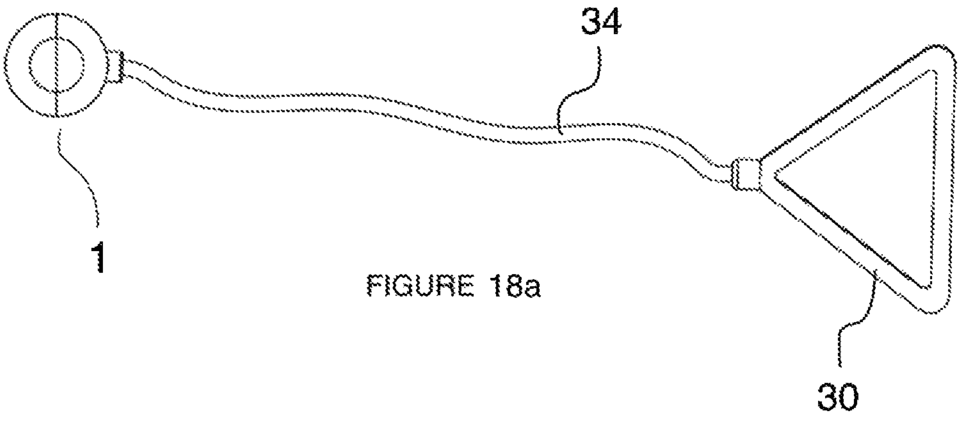
FIGS. 18*a* to 18*c* show plan (FIG. 18*a*), under plan (FIG. 18*c*) and a side view (FIG. 18*b*) of the device, the flexible connector and the handle.
Figure 18B:
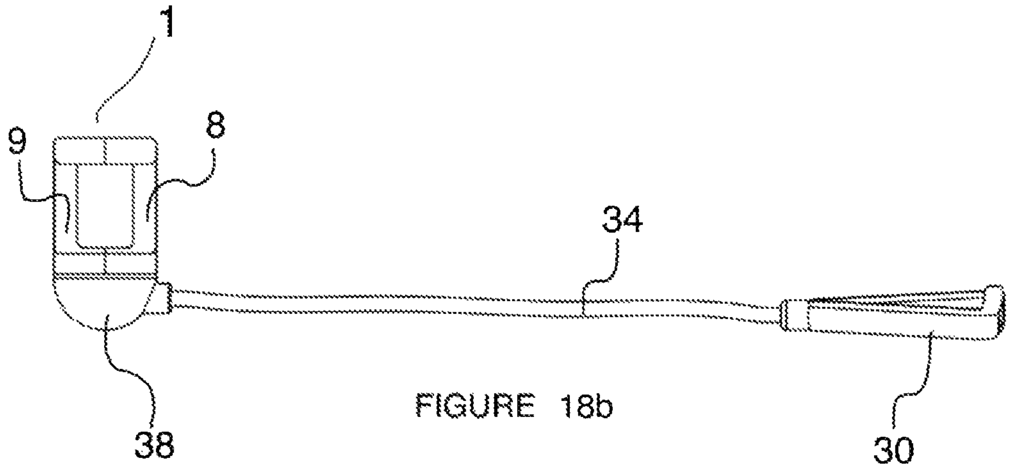
Figure 18C:
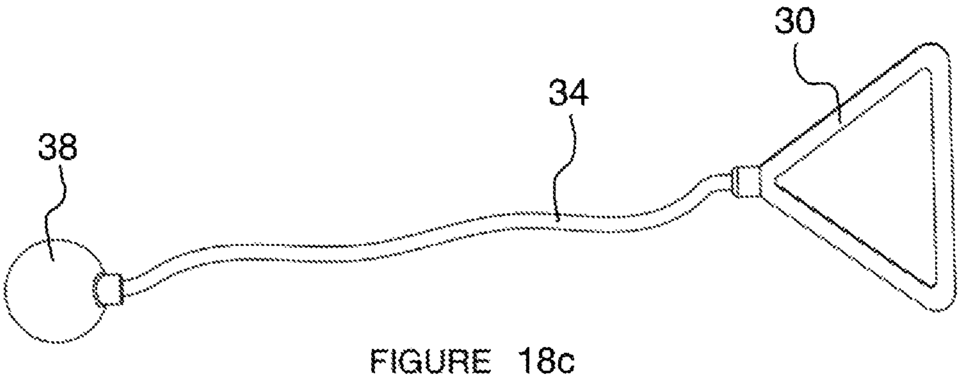

FIG. 16 is a close up view of a modified cage showing forward cage portion 9 and rearward cage portion. The phallus or appendage 36 is connected to the cage 14 by way of a connection means shown in greater detail in FIGS. 20*a* and 20*b* for example. FIG. 17 shows the device 1 deployed and hanging from the scrotum 3 and the location of the appendage (male phallus 36), the flexible connector 34 and the handle 30.

FIGS. 18*a* to 18*c*, 19*a* and 19*b* show various views of the device 1, the flexible connector 34 and the handle 30.

Figure 20A:
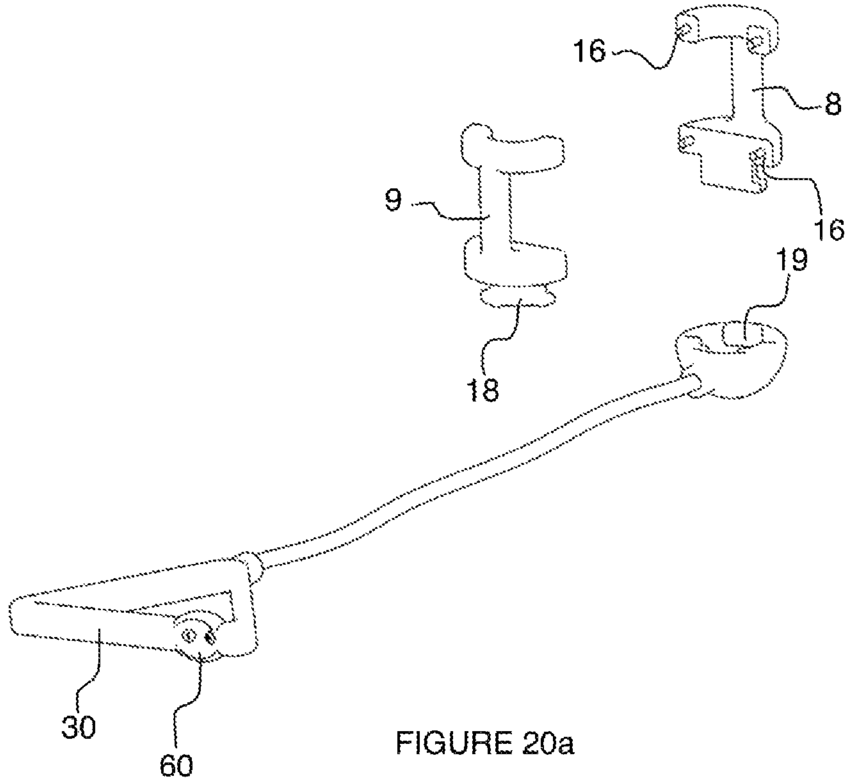
FIGS. 20*a* and 20*b* show overall views of the device disconnected from the flexible connector and the handle, with the two-part cage disassembled.
Figure 20B:
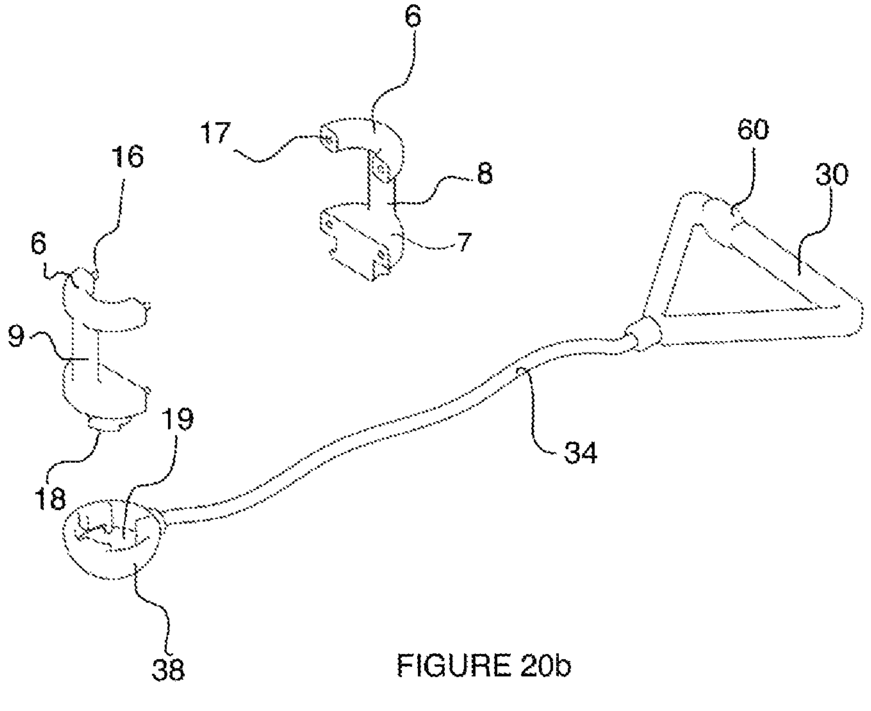
Figure 21A:
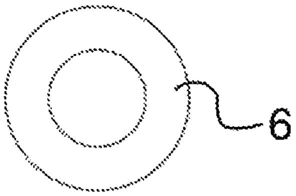
FIGS. 21*a* to 21*f* show plan (FIGS. 21*a* and 21*d*), elevational (FIGS. 21*c* and 21*e*) and overall views (FIGS. 21*b* and 21*f*) of a further embodiment of the device that is formed as a single shot product.
Figure 21B:
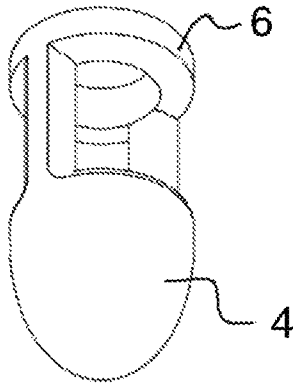
Figure 21C:
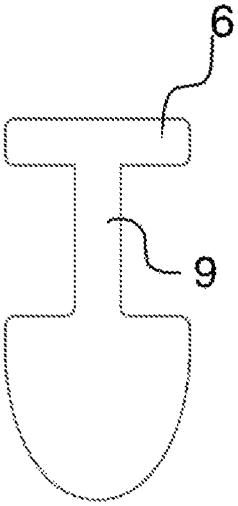
Figure 21E:
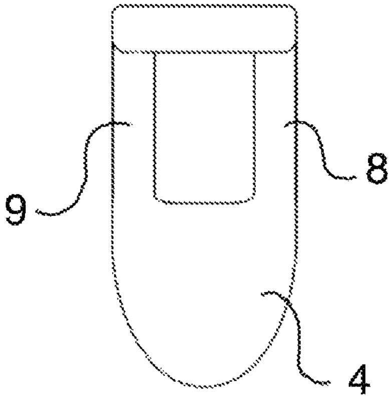
Figure 21D:
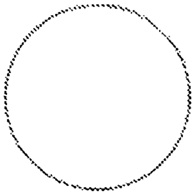
Figure 21F:
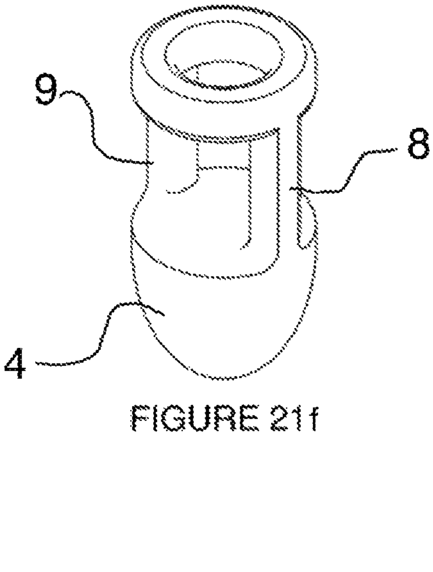
Figure 22A:
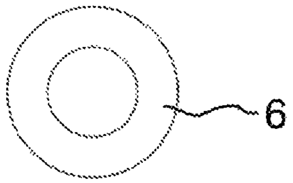
FIGS. 22*a* to 22*f* show views of an alternative embodiment of the device, in plan view (FIGS. 22*a* and 22*e*), elevational views (FIGS. 22*c* and 22*d*) and overall views (FIGS. 22*b* and 22*f*) formed as a two part mould, which has a removable bulbous tip.
Figure 22B:
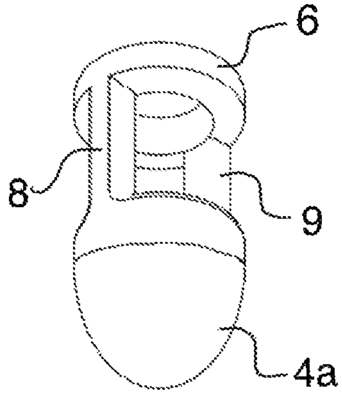
Figure 22C:
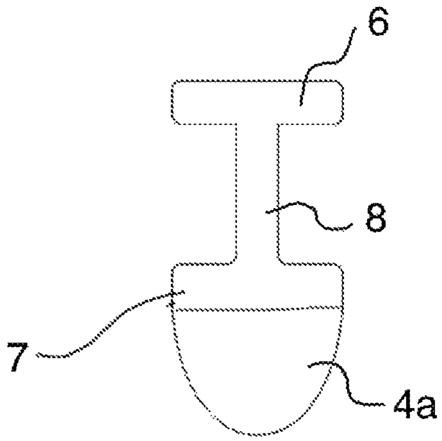
Figure 22D:
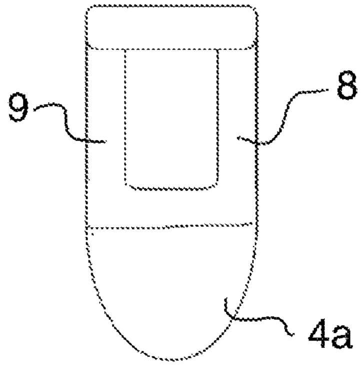
Figure 22E:
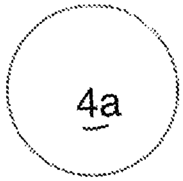
Figure 22F:
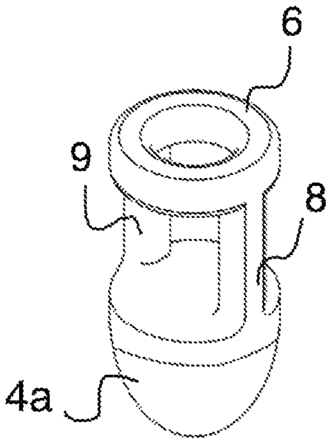
Figure 24A:
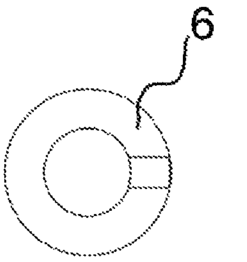
FIGS. 24*a* to 24*f* show views of an alternative embodiment of the device, with a cut-out opening, formed as a single mould and show above and under plan views (FIGS. 24*a* and 24*e*), overall views (FIGS. 24*b* and 24*f*) from above and below and side elevations (FIGS. 24*c* and 24*d*)
Figure 24B:
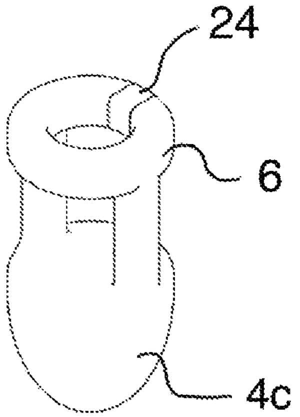
Figure 24C:
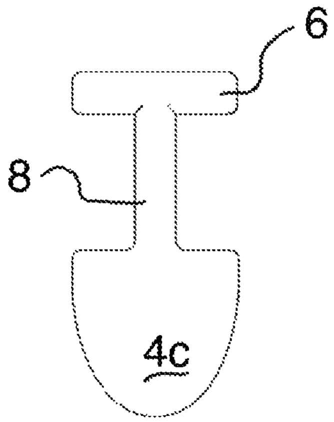
Figure 24D:
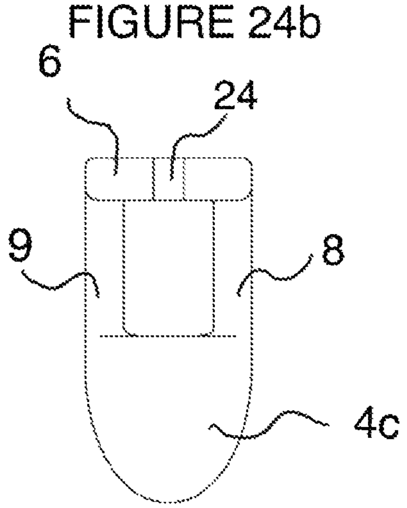
Figure 24E:
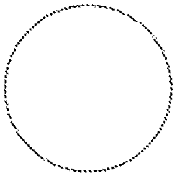
Figure 24F:
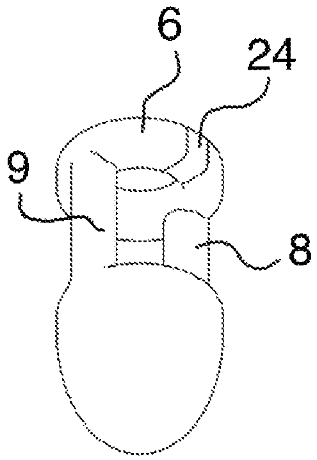

FIGS. 20*a* and 20*b* show overall views, from above and below, of the device 1 disconnected from the flexible connector 34 and the handle 30, with the two-part cage 14 when disassembled. A cable connector 38 is also shown for connecting the flexible connector 34 to the body portion or cage 14 of the device 1. Optionally the cable connector 38 is detachable from the body portion, as shown for example in FIG. 20*b*.

Referring to FIG. 20*a* there is shown a control means 60 which is provided on or in the handle 30 which controls a vibrator or vibrating means (not shown) or other stimulator (not shown) so as to further increase stimulation to the wearer and their sexual partner. The vibrating means or other stimulator is optionally housed in a penis extension or phallus 36 or it may be formed integrally with the cage and the housing 38 of the cable connector or the vibrating means or other stimulator may be supplied as a separate item. The vibrating means or other stimulators can enhance stimulation of the vagina, labia and clitoris and thereby improve sensations during intercourse. Furthermore they may also stimulate the wearer's penis and so help it to become and remain erect, for example as shown in FIG. 17.

The fact that the vibrating means or other stimulator is controllable by one person by way of the handle and another person by way of a remote control device enables, for example people of limited mobility to partake in sexual intercourse and intimate physical activity as they are able to speak commands to a suitably configured mobile communications device which communicates with and controls the vibrating means or other stimulator.

Referring to FIGS. 21 to 33 there are shown different views of various embodiments of appendages formed integrally with or attachable to the body portion 2. These are depicted as resembling a male appendage. Optionally the appendage may take a number of sizes and shaped items, such as for example ribbed spheres, first shapes, novelty characters (real or cartoon).

Appendages may comprise rigid inner components over which a softer material, such as a flexible synthetic rubber is over moulded. Therefore the embodiments shown may have a hard synthetic plastics inner core that is over moulded by a softer material such as polymer (TPG) or silicone rubber.

Advantages of the embodiments shown in FIGS. 21 to 33 are similar to the embodiment shown in FIG. 1 however these embodiments include features that ease the insertion of the testicles into the cage 14. In addition some of these versions depicted have reduced numbers of moulded parts which reduces their production cost so as to enable an inexpensive range of products.

In some embodiments the device 1 has stretchy interconnects 8 and 9 which may be formed from a single silicone moulding without a rigid synthetic plastics core. Such an embodiment enables the user to insert his testicles into the cage 14 by stretching the rear containment ring and by urging his testicles into the space therein defined.

When formed form a flexible silicone material the cage 14 is sufficiently resilient to facilitate insertion of the testicles, whilst ensuring the cage remains hanging from the scrotum during intercourse.

It is appreciated that where separate items are adapted to be used as part of a kit a range of different features or materials or dimensioned to suit the users' preferences.

In this variation, a preferred embodiment has been reduced to two mouldings, the largest, a one piece cage incorporating the tip has a small segment of the bottom ring removed of 12 mm or thereabouts. In this small cut out the upper skin or the scrotum septum can be pushed through, to allow the testicles to be inserted in the cage.

The small missing or cut out insert or segment 25 is a separate moulding that fits into cut-out opening 24 to complete the upper ring portion 6. This segment may be held in place by magnets, push fit, slide in fit, retained with sprung ball bearings (not shown), or may be screwed in push fitted into place for example.

Figure 30A:
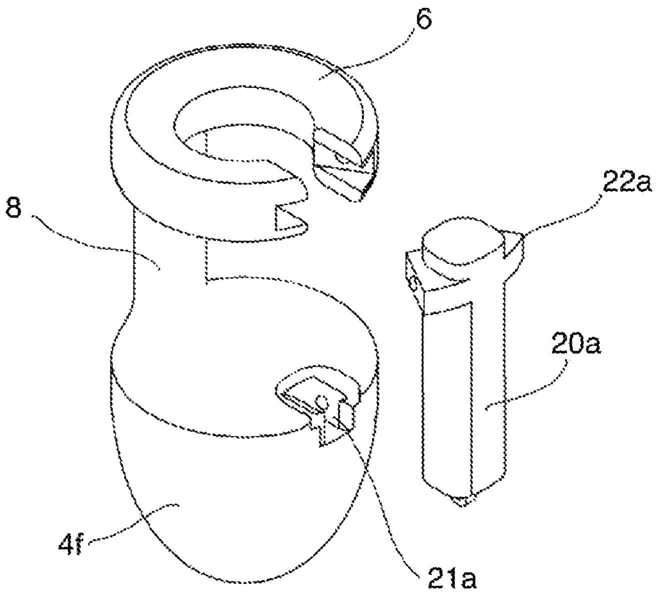
FIGS. 30*a* and 30*b* show overall views of an alternative engagement mechanism which locks by way of a ball bearing spring lock.

In a second embodiment the device 1 has a removable interconnect 20*a* as shown for example in FIG. 30*a* which enables a user to insert a testicle and/or his entire scrotum and afterwards replace the interconnect 20*a* and thereby attach the device 1 to the scrotum, as shown in FIG. 17.

In a first preferred embodiment the cage, one of the two interconnects are hinged or completely removable. This configuration allows the interconnect to open up to 90 degrees or completely removed to allow the skin above the scrotum to be pushed through an opening which is typically 10-20 mm and more preferably 10-15 mm.

Within this range the testicles are received can be neatly placed in the cage. The hinged or removed interconnect is then lowered back down, and its locking mechanism, as depicted secures it in place. The top of the hinge (or both ends of completely removable interconnect) can be held in place by magnets, push fit, slide in fit, retained with sprung ball bearings against recesses or be screwed in place for example.

FIGS. 21*a* to 21*f* show plan (21*a* and 21*d*), elevational (21*c* and 21*e*) and overall views (21*b* and 21*f*) of a further embodiment of the device that is formed as a single shot product.

FIGS. 22*a* to 22*f* show views of an alternative embodiment of the device, in plan view (22*a* and 22*e*), elevational views (22*c* and 22*d*) and overall views (22*b* and 22*f*) formed as a two part mould, which has a removable bulbous tip.

FIGS. 23*a* to 23*f* show views of an alternative embodiment of the device, formed as a two part mould with a removable tip and shows overall views (23*a* and 23*b*) from below and (23*c*) from above, the Figures show interconnection means which connect the tip to the cage.

FIGS. 24*a* to 24*f* show views of an alternative embodiment of the device, with a cut-out opening, formed as a single mould and shows above and under plan views (24*a* and 24*e*), overall views (24*b* and 24*f*) from above and below and side elevations (24*c* and 24*d*).

Figure 25A:
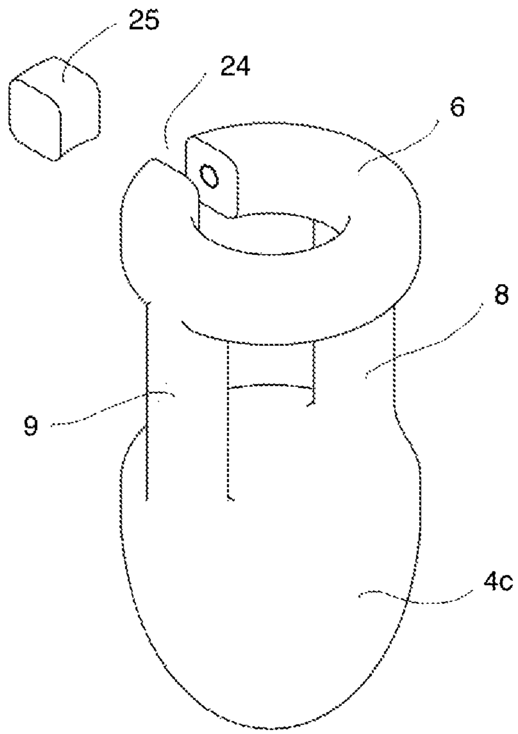
FIGS. 25*a* and 25*b* show overall views from above and below of the embodiment shown in FIGS. 24*a* to 24*f* and depict the cut-out opening and cut-out insert.
Figure 25B:
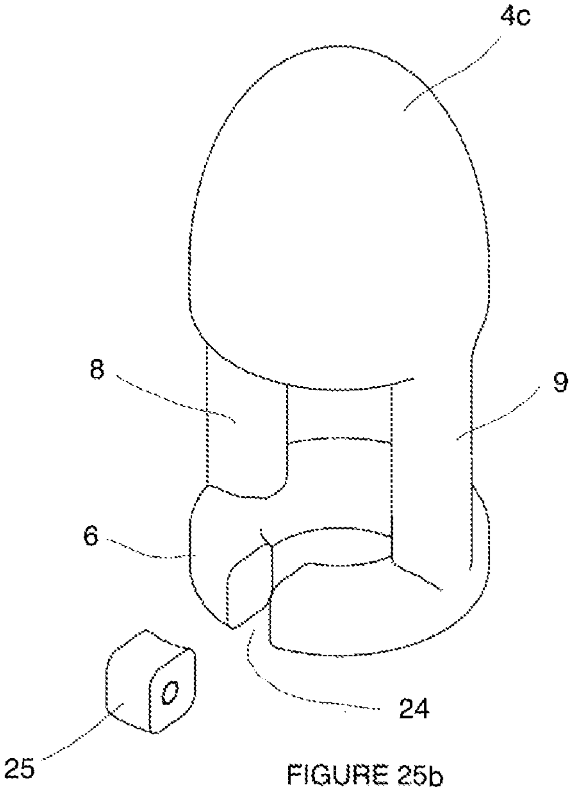
Figure 26A:
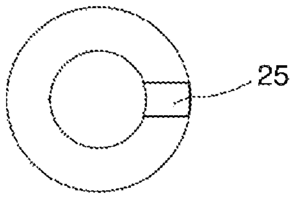
FIGS. 26*a* to 26*f* show views of an alternative embodiment of the device which is in two part form, with a cut-out opening, formed as a single mould and shows above and under plan views (FIGS. 26*a* and 26*e*), overall views (FIGS. 26*b* and 26*f*) from above and below and side elevations (FIGS. 26*c* and 26*d*)
Figure 26B:
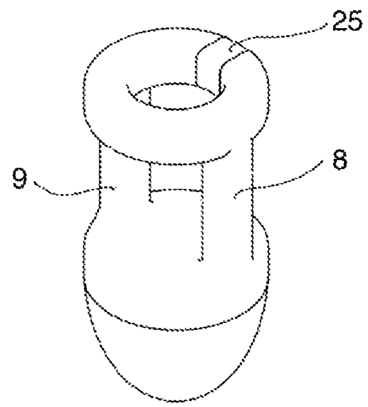
Figure 26C:
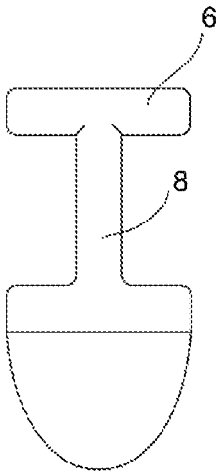
Figure 26D:
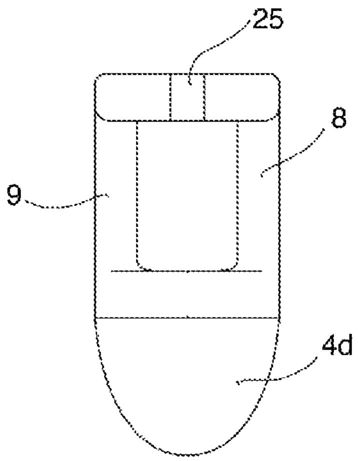
Figure 26E:
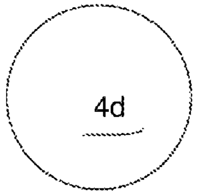
Figure 26F:
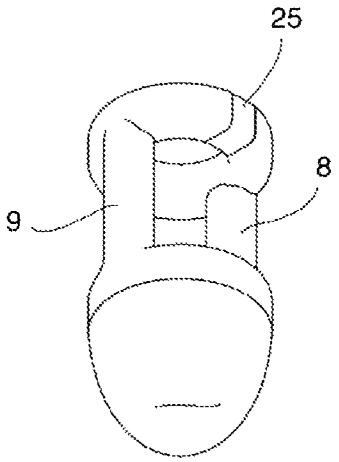

FIGS. 25*a* and 25*b* show overall views from above and below of the embodiment shown in FIGS. 24*a* to 24*f* and depict the cut-out opening and cut-out insert.

FIGS. 26*a* to 26*f* show views of an alternative embodiment of the device which is in two part form, with a cut-out opening, formed as a single mould and shows above and under plan views (26*a* and 26*e*), overall views (26*b* and 26*f*) from above and below and side elevations (26*c* and 26*d*).

Figure 27A:
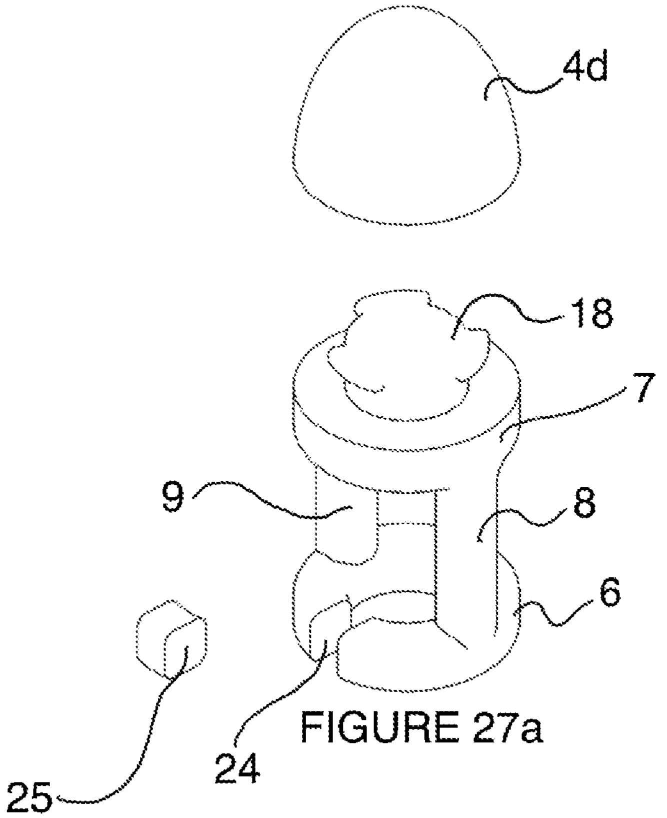
FIGS. 27*a* and 27*b* show overall views of the device, which is in two part form, of the embodiment shown in FIGS. 26*a* to 26*f* and depict the cut-out opening and cut-out insert.
Figure 27B:
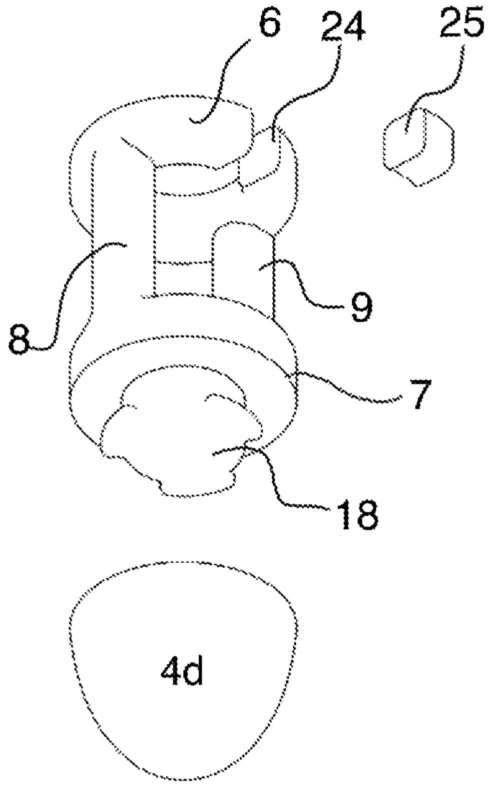
Figure 28A:
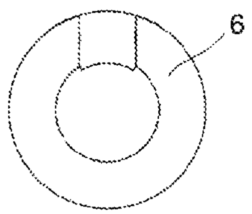
Figure 28B:
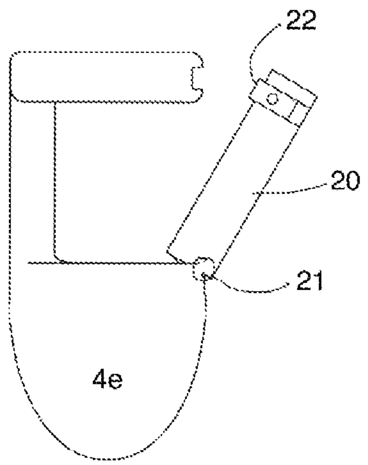
Figure 28C:
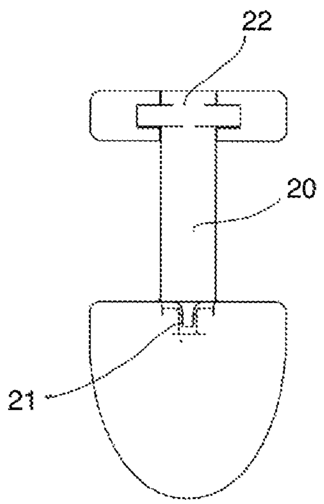
Figure 28D:
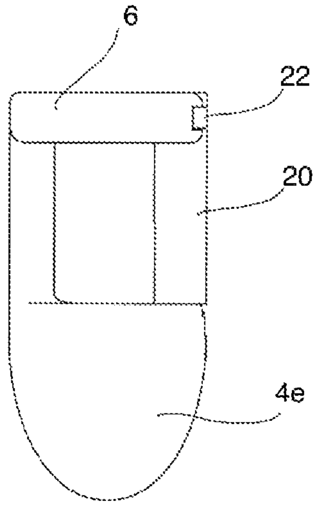
Figure 28E:
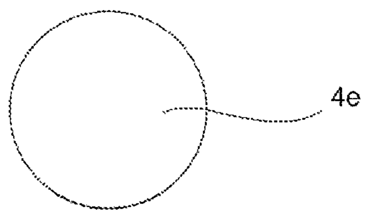
Figure 29A:
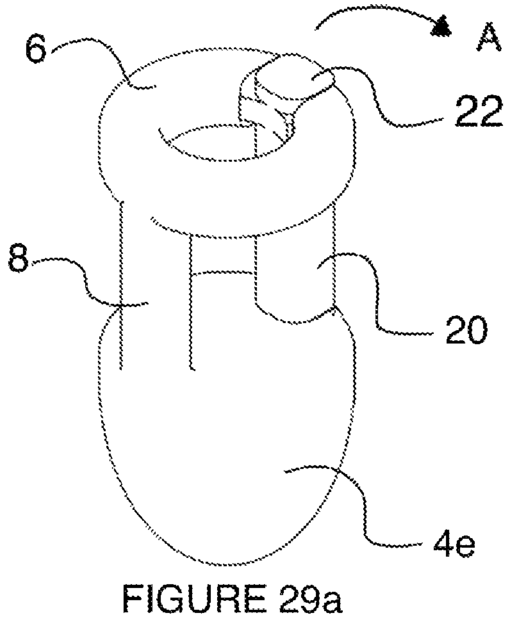
FIGS. 29*a* to 29*d* show overall views of the device of FIG. 28 from above (FIG. 29*a*) and below (FIGS. 29*b* to 29*d*) and depict the hinged connector in an open and closed configuration in direction of arrow A and arrow B in FIG. 29*c;*
Figure 29B:
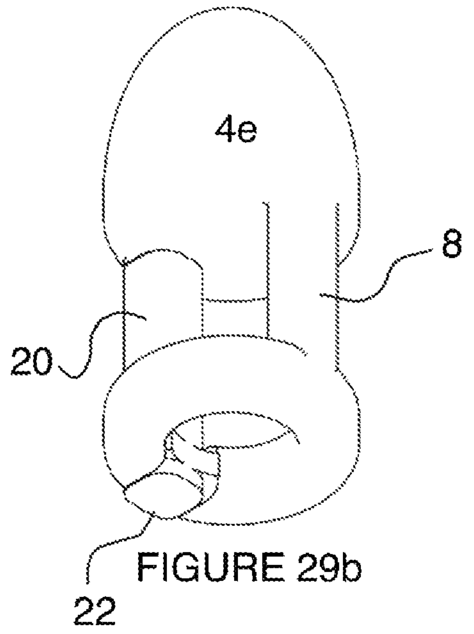
Figure 29C:
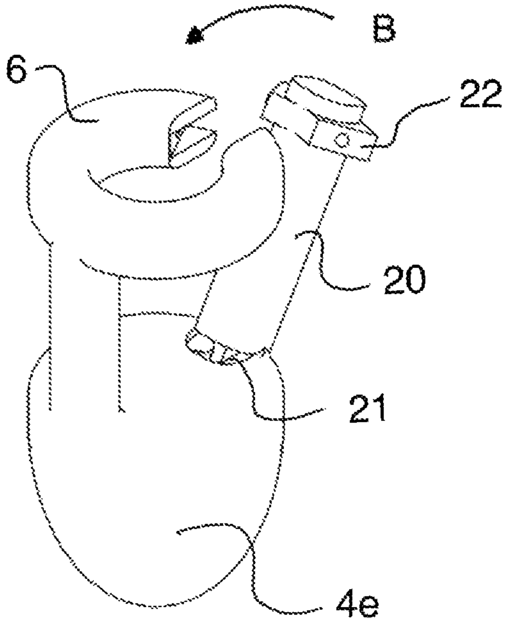
Figure 29D:
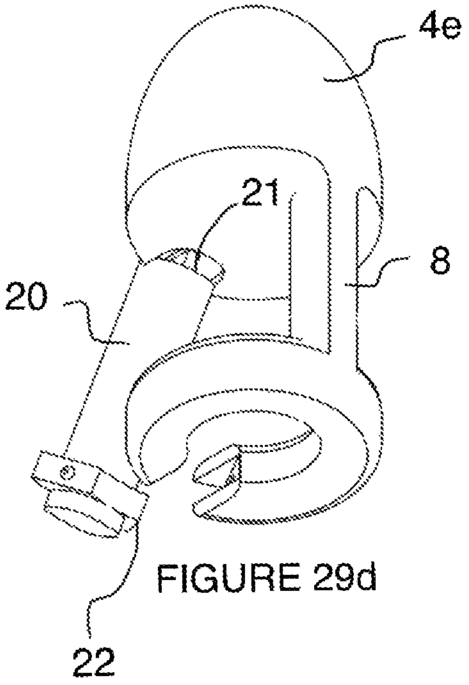

FIGS. 27*a* and 27*b* show overall views of the device, which is in two part form, from above and below of the embodiment shown in FIGS. 26*a* to 26*f* and depict the cut-out opening and cut-out insert.

FIGS. 28*a* to 28*f* show views of an alternative embodiment of the device with a hinged connector as part of the cage, formed as a single mould and shows above and under plan views (28*a* and 28*e*), side elevation view showing the hinged connector (28*b*) and side elevations (28*c* and 28*d*).

FIGS. 29*a* to 29*d* show overall views of the device of FIG. 28 from above (29*a*) and below 29*b* to 29*d*) and depict the hinged connector in an open and closed configuration in direction of Arrow A and arrow B.

In another embodiment the cage may be curved or adjustable to suit different sized users especially where there may be a significant difference in physical sizes between each partner. Such an adjustable cage may include a hinge which may be an over moulded synthetic plastics hinge or so called 'living hinge' or one which over moulds a malleable former with a softer silicone outer. So that a former is able to be bent to a particular angle to suit both partners and remains in that configuration during intercourse.

Figure 30B:
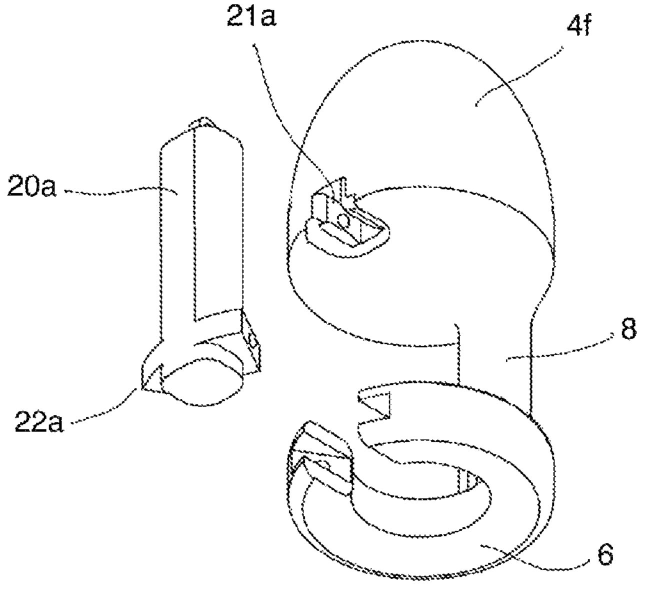
Figure 31A:
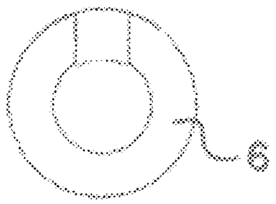
FIGS. 31*a* to 31*e* show views of the alternative embodiment of the device shown in FIG. 30 with removable connector as part of the cage, formed as a single mould and shows above and under plan views (FIGS. 31*a* and 31*e*), side elevation view showing the hinged connector (FIG. 31*b*) and side elevations (FIGS. 31*c* and 31*d*)
Figure 31B:
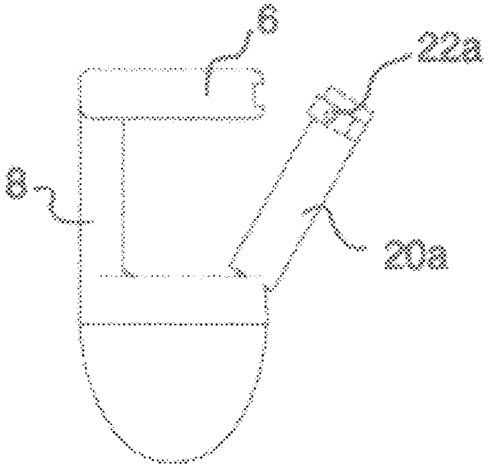
Figure 31C:
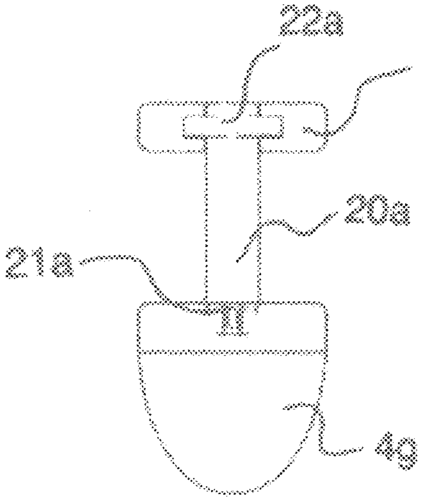
Figure 31D:
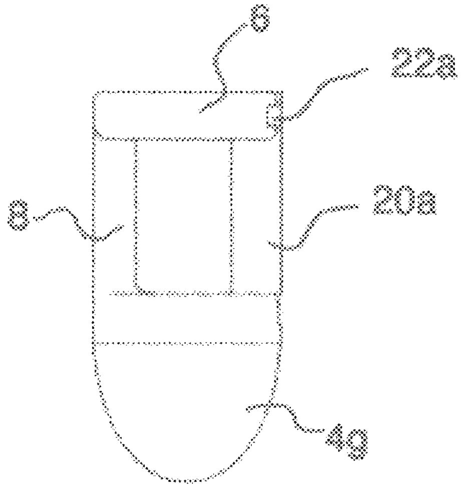
Figure 31E:
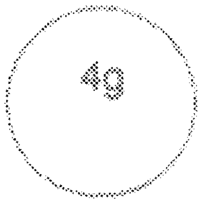
Figure 32A:
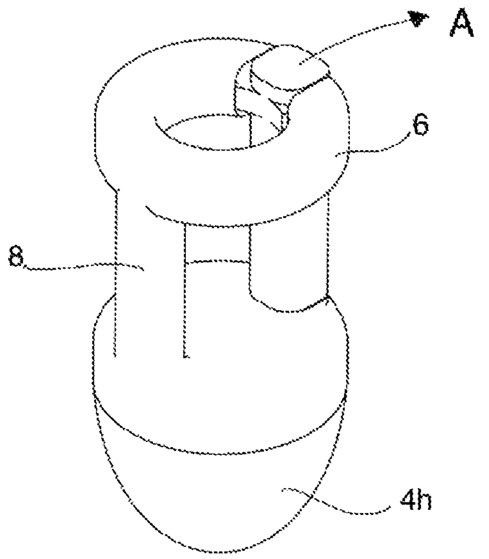
FIGS. 32*a* to 32*d* show overall views of an alternative engagement mechanism which opens by way of a pivot and a locks by way of a ball bearing spring lock.
Figure 32B:
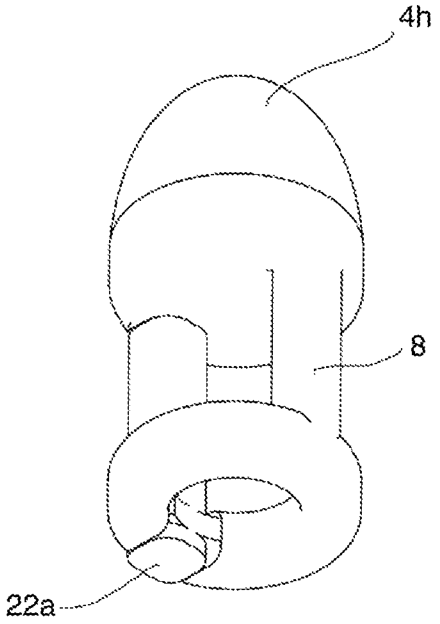
Figure 32C:
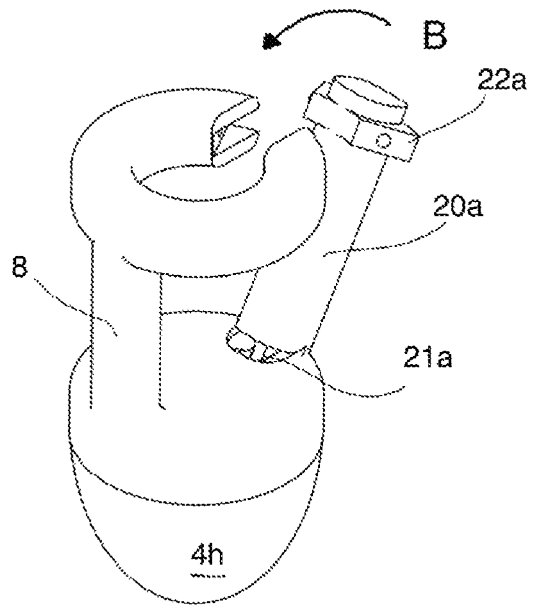
Figure 32D:
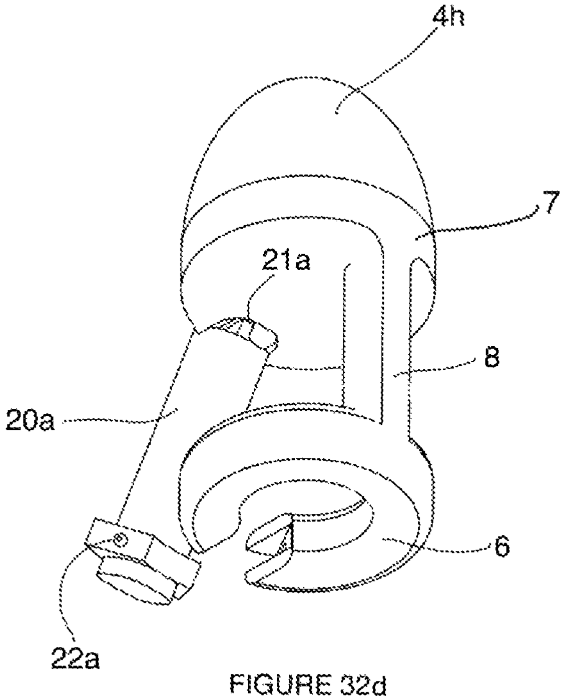

FIGS. 30*a* and 30*b* show overall views of a single shot device with an engagement mechanism which locks using a ball bearing spring lock.

FIGS. 31*a* to 31*e* show views of the alternative embodiment of the device shown in FIG. 30 with removable connector as part of the cage, formed as a single mould and shows above and under plan views (28*a* and 28*e*), side elevation view showing the hinged connector (28*b*) and side elevations (28*c* and 28*d*).

FIGS. 32*a* to 32*d* show overall views of an alternative engagement mechanism which opens by way of a pivot and a locks by way of a ball bearing spring lock.

Figure 33A:
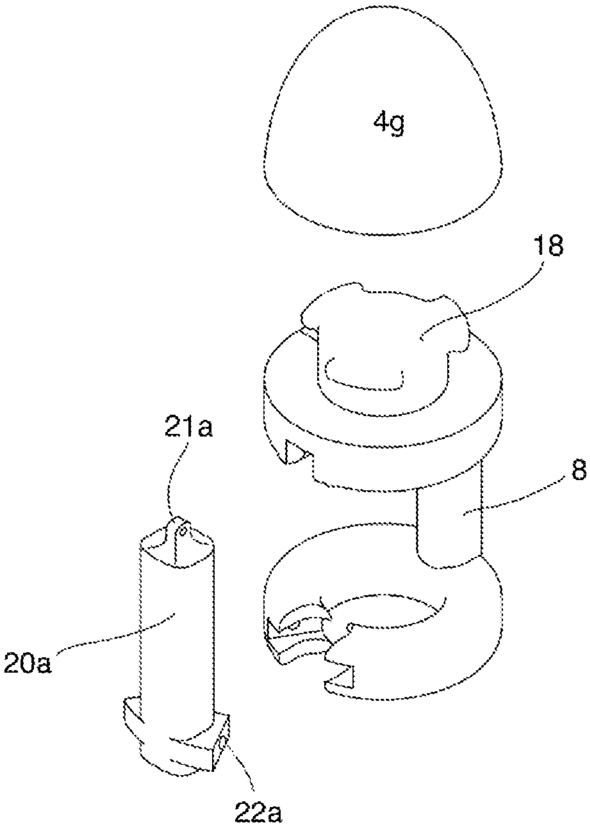
FIGS. 33*a* and 33*b* show view of an alternative embodiment of the device with a removable connector as part of the cage, with a removable bulbous end and shows a removable connector (33*b*).
Figure 33B:
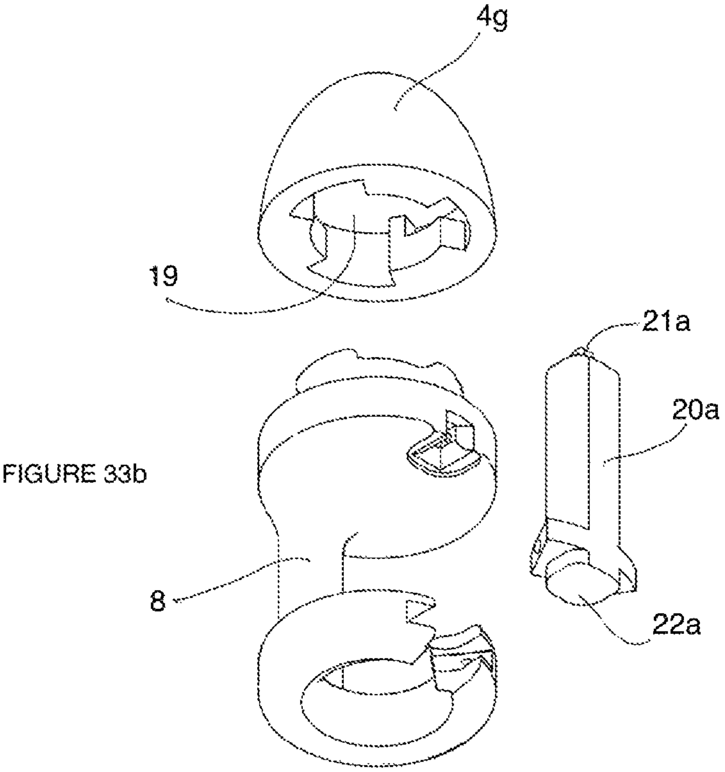

FIGS. 33*a* and 33*b* show view of an alternative embodiment of the device with a removable connector as part of the cage, with a removable bulbous end and shows a removable connector (33*b*). The vibrating means is provided in the body portion or in a phallus and includes a battery or preferably a rechargeable battery which is housed within a sealed container in the body portion. In one embodiment a wireless receiver is connected to the vibrating means and receives a command signal to actuate the vibrating means and/or control its speed and/or select a mode of operations, such as fast, slow, pulse, intermittent or random modes.

A user is able to vary speed and/or intensity of the vibrating means by way of a wired or wireless remote control means or simply by applying tension to the connector. The remote control means may be wired, or wireless and a further speed or mode control means may be provided. Again electro stimulators may be provided as optional features which are operable via an Internet connection and suitable remote monitoring and control means are operable to control the application and timing of stimulating currents. Ideally the mobile communications device is configured to be operable via an Internet connection and a wireless transmitter is in operable communication to relay a command or request, from a remote location, to actuate the vibrator and/or electro stimulator.

In another embodiment a connection means 34, such as cord, chain, flexible extender or a plurality of stiff rods hinged one to another, is provided for connecting the body portion to a handle 30. Referring to FIG. 15 for example, the handle 30 is therefore able to be used by the user's partner or the wearer in order to assist in intercourse by gently pulling the connection means 34, thereby applying tension to the connection means and urging the phallus 36 and thereby the body portion to assist with penetration.

To simulate normal sexual thrusting movements in order to stimulate the vagina, bulbous end 4, which is attached to the lower portion 7 of the cage 6, may be pulled by the handle 30. An optional connector may be used to attach a clitoris tickler or stimulator so that it rubs against the clitoris. The pulling of the handle 30 draws the cage towards the vagina and thrusts the phallus 36 harder into the vagina in order to stimulate the vagina under direct control of the person pulling the handle.

Figure 19A:
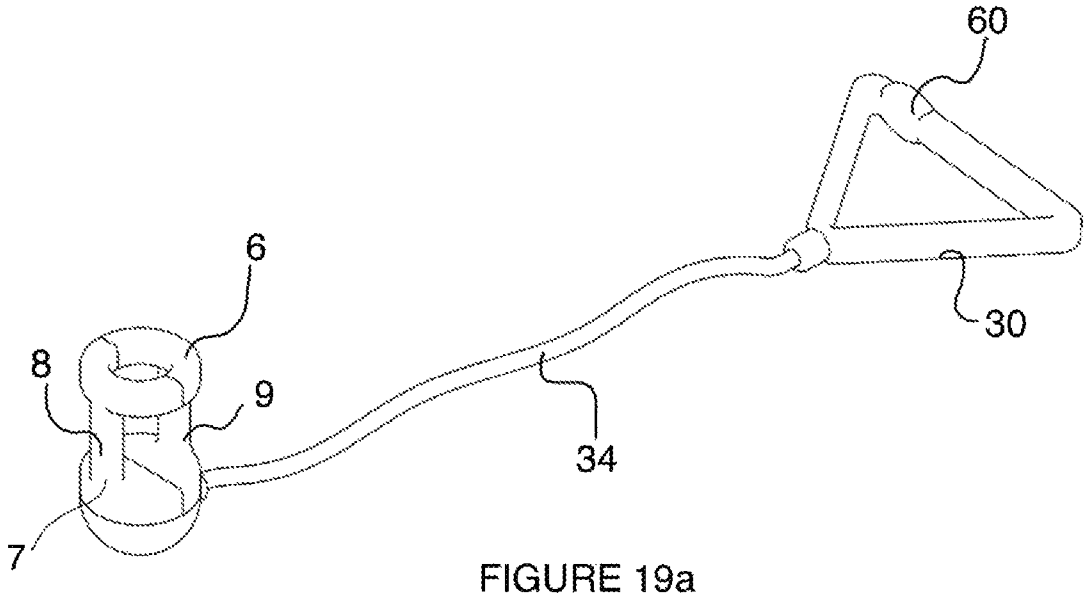
FIGS. 19*a* and 19*b* show overall views from above (19*a*) and below (19*b*) of the device connected to the flexible connector and the handle.
Figure 19B:
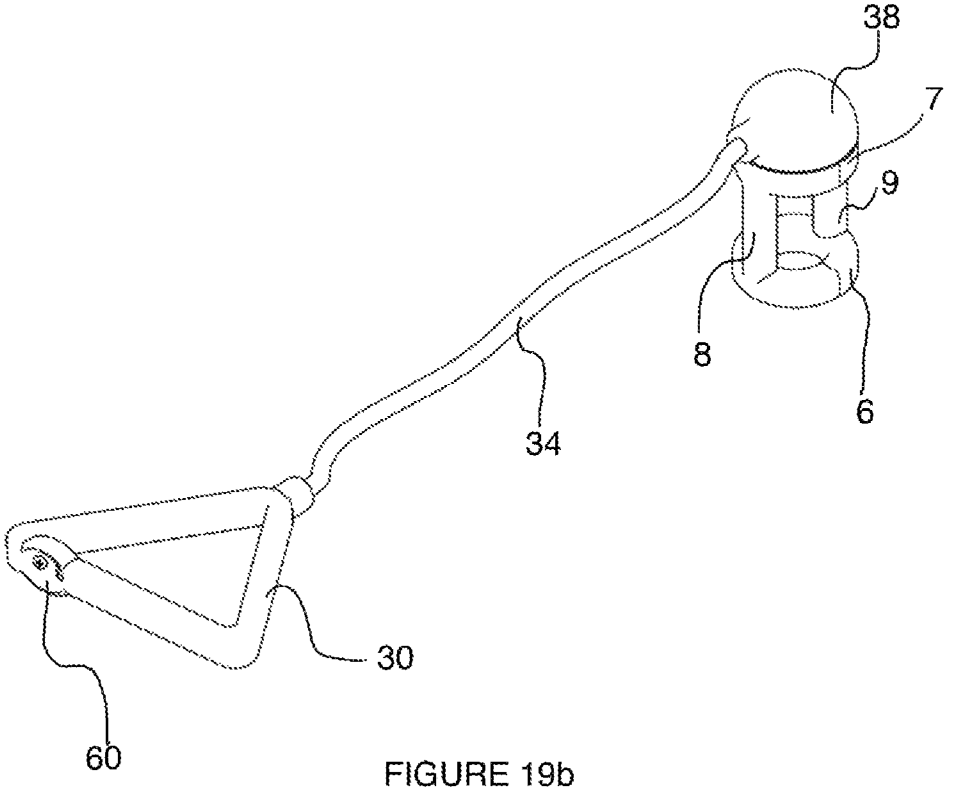

In the embodiment shown in FIGS. 19*a* and 19*b* a control button 60 is located on the handle which controls a vibrator or electrostimulation (not shown) which may be housed in the phallus 36 or end cap 38 or both.

It is to be understood that the device of the present invention may be used for other applications and as such is not to be limited to treatment of erectile dysfunction. For example, the device could in some embodiments be used as a sex aid in such embodiments additional features may be included in the attachment such as one or more vibrating and/or electro stimulating devices, as mentioned above, as well as movable parts which expand and contract the girth of the attachment device.

Ideally attachment devices, connectors and tethers are detachable so that they may be disassembled and taken apart for cleaning or removed for separate sale, stowage or for recharging.

The invention has been described by way of examples only and it will be appreciated that variation may be made to the embodiments without departing from the scope of protection as defined by the claims.

LIST OF PARTS

1 device
2 body portion
3 scrotum
4 bulbous portion
5*a* lockable engagement devices
5*b* lockable engagement devices
6 upper portion

7 lower portion
8 forward connector
9 aft connector
12*a* right testicle
12*b* left testicle
14*a* forepart of cage
14*b* aft part of cage
16 pips
17 recesses
18 twist lock comprising 5*a* and 5*b*
19 twist lock recess in end cap
20 hinged connector
21 hinge
22 snap lock
24 cut-out opening
25 cut-out insert or segment
30 handle
34 flexible connector
36 phallus
37*a* first side interconnect
37*b* second side interconnect
38 cable connector housing or cap
60 control button
70 wireless receiver
80 wireless transmitter
90 mobile communications device
99 microphone
100 display

The invention claimed is:

1. A device for attachment to a scrotum, the device comprising:

a cage having an upper portion which is configured to surround a scrotal septum and two connectors which connect the upper portion to a lower portion and define separate lateral openings through which a left and a right testicle can protrude, the two connectors being configured to lie in a same plane as a wearer's scrotal raphe when the cage hangs from the scrotal septum; and a body portion that extends from the lower portion shaped to resemble a male appendage.

2. The device according to claim 1 wherein the body portion is removably connectable to/from the lower portion by way of a connection means.

3. The device according to claim 2 wherein the connection means is selected from the group comprising: a threaded interconnect, a twist lock interconnect, a push-fit interconnect, a snap fit interconnect and a magnetic interconnect.

4. The device according to claim 1 wherein the upper portion is in the form of a circular ring.

5. The device according to claim 1 wherein the two connectors which connect the upper portion to the lower portion are rigid.

6. The device according to claim 1 wherein at least one of the connectors is connected by way of a hinge to at least the upper portion or the lower portion so as to assist in placing the device around the scrotal septum.

7. The device according to claim 1 wherein at least one of the connectors is removably connected to at least the upper portion or the lower portion so as to assist in location of the device around the scrotal septum.

8. The device according to claim 1, in which a side connector is provided for connection to a phallus or penis shaped portion.

9. The device according to claim 8, further comprising: a universal joint or other flexible joint means for varying an orientation of the phallus or penis shaped portion to a desired angle of deployment through a range of angles between 45 degrees above and below a wearer's erect penis.

10. The device according to claim 8, in which a vibrating means and/or electro stimulating means is provided in the phallus or penis shaped portion.

11. The device according to claim 1 wherein the upper and lower portions of the device and at least one of the connectors is formed from a flexible material.

12. The device according to claim 11 wherein the upper and lower portions and at least one of the connectors are formed as a single injection moulded item.

13. The device according to claim 1 wherein the cage and/or the body portion is adapted to receive a tickler or clitoral stimulator.

14. The device according to claim 1 wherein a side connector or flexible tether is provided for connecting a handle to the body portion of the device.

15. The device according to claim 14 wherein the body portion comprises at least one inflatable portion which is configured to be inflated or deflated in order to adjust its dimensions.

16. The device according to claim 14, in which a vibrating means and/or electro stimulating means is provided in an end cap or housing to which the connector or flexible tether is connected.

17. The device according to claim 1, in which a vibrating means and/or electro stimulating means is provided in the body portion of the device.

18. A device for attachment to a scrotum, the device comprising:

a cage having an upper portion which is configured to surround a scrotal septum and two connectors which connect the upper portion to a lower portion and define separate lateral openings through which a left and a right testicle can protrude, the two connectors being configured to lie in a same plane as a wearer's scrotal raphe when the cage hangs from the scrotal septum; and a body portion that extends from the lower portion, wherein the body portion extending from the lower portion of the device is bulbous shaped.

19. A device for attachment to a wearer's scrotum comprising an outer cage that comprises two or more portions that are separable and reconnectable, the two or more portions have first and second opposable ends and at least one pair of opposable side portions extending therebetween, the cage being configurable between: a first open configuration, in which the at least one pair of opposable side portions are separated from each other to define a cavity which receives the scrotum; and a second closed configuration in which the at least one pair of opposable side portions of the cage contact with each other to thereby surround the wearer's scrotal septum, wherein at least one of the two or more portions include an extending body portion shaped to resemble a male appendage.

* * * * *